(12) United States Patent
Weerakoon et al.

(10) Patent No.: US 12,377,273 B2
(45) Date of Patent: Aug. 5, 2025

(54) CIRCUITRY TO ASSIST WITH NEURAL SENSING IN AN IMPLANTABLE STIMULATOR DEVICE IN THE PRESENCE OF STIMULATION ARTIFACTS

(71) Applicant: Boston Scientific Neuromodulation Corporation, Valencia, CA (US)

(72) Inventors: Pujitha Weerakoon, Valencia, CA (US); Goran N. Marnfeldt, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 387 days.

(21) Appl. No.: 18/060,344

(22) Filed: Nov. 30, 2022

(65) Prior Publication Data

US 2023/0173273 A1   Jun. 8, 2023

Related U.S. Application Data

(60) Provisional application No. 63/264,821, filed on Dec. 2, 2021.

(51) Int. Cl.
| A61N 1/36 | (2006.01) |
| A61N 1/378 | (2006.01) |
| H03F 3/45 | (2006.01) |

(52) U.S. Cl.
CPC ..... *A61N 1/36125* (2013.01); *A61N 1/36135* (2013.01); *A61N 1/3782* (2013.01); *H03F 3/45264* (2013.01)

(58) Field of Classification Search
CPC ............ A61N 1/36125; A61N 1/36135; A61N 1/3782; A61N 1/36062; A61N 1/08; A61B 5/7203; A61B 5/7225
See application file for complete search history.

(56) References Cited

U.S. PATENT DOCUMENTS 4,677,986 A   7/1987   Decote, Jr.
5,697,958 A   12/1997  Paul et al.
(Continued)

FOREIGN PATENT DOCUMENTS

EP        1147784      10/2001
WO    2015/077362      5/2015
(Continued)

OTHER PUBLICATIONS

U.S. Appl. No. 63/263,318, filed Oct. 29, 2021, Marnfeldt.
(Continued)

*Primary Examiner* — Paula J Stice
(74) *Attorney, Agent, or Firm* — Lewis & Reese, PLLC

(57) ABSTRACT

Sense amplifier (amp) circuitry for an implantable stimulator device is disclosed useful for sensing neural responses or other voltages in a patient's tissue. The sense amp circuitry comprises a low-voltage and a high-voltage sense amp circuit, either of which may be selected based on an assessment of the magnitude of the voltage at either or both of the inputs connected to selected sensing electrodes. The assessed magnitude, as determined by monitoring circuitry, can be processed by an algorithm to select use of one of the sense amp circuits, selecting the low-voltage sense amp circuit when the magnitude(s) are lower, and the high-voltage sense amp circuit when the magnitude(s) are higher. Furthermore, DC offset compensation circuitry is disclosed to equate the DC levels of the inputs, which may only operate when the high-voltage sense amp is selected.

20 Claims, 9 Drawing Sheets

(56) References Cited

U.S. PATENT DOCUMENTS

| | | | |
|---|---|---|---|
| 5,702,429 A | 12/1997 | King | |
| 5,902,236 A | 5/1999 | Iversen | |
| 5,902,249 A | 5/1999 | Lyster | |
| 5,913,882 A | 6/1999 | King | |
| 6,181,969 B1 | 1/2001 | Gord | |
| 6,516,227 B1 | 2/2003 | Meadows et al. | |
| 7,024,247 B2 | 4/2006 | Gliner et al. | |
| 7,424,322 B2 | 9/2008 | Lombardi et al. | |
| 7,450,992 B1 | 11/2008 | Cameron | |
| 8,255,057 B2 | 8/2012 | Fang et al. | |
| 8,335,664 B2 | 12/2012 | Eberle | |
| 8,352,030 B2 | 1/2013 | Denison | |
| 8,606,362 B2 | 12/2013 | He et al. | |
| 8,620,436 B2 | 12/2013 | Parramon et al. | |
| 9,044,155 B2 | 6/2015 | Strahl | |
| 9,155,892 B2 | 10/2015 | Parker et al. | |
| 9,248,274 B2 | 2/2016 | Troosters et al. | |
| 9,248,279 B2 | 2/2016 | Chen et al. | |
| 9,259,574 B2 | 2/2016 | Aghassian et al. | |
| 9,265,431 B2 | 2/2016 | Hincapie Ordonez et al. | |
| 9,302,112 B2 | 4/2016 | Bornzin et al. | |
| 9,381,356 B2 | 7/2016 | Parker et al. | |
| 9,386,934 B2 | 7/2016 | Parker et al. | |
| 9,403,013 B2 | 8/2016 | Walker et al. | |
| 9,409,020 B2 | 8/2016 | Parker | |
| 9,526,897 B2 | 12/2016 | Chen et al. | |
| 9,533,148 B2 | 1/2017 | Carcieri | |
| 9,731,116 B2 | 8/2017 | Chen | |
| 9,872,990 B2 | 1/2018 | Parker et al. | |
| 9,974,455 B2 | 5/2018 | Parker et al. | |
| 10,076,667 B2 | 9/2018 | Kaula et al. | |
| 10,716,937 B2 | 7/2020 | Feldman et al. | |
| 10,792,491 B2 | 10/2020 | Feldman et al. | |
| 10,881,859 B2 | 1/2021 | Brill et al. | |
| 11,040,202 B2 | 6/2021 | Marnfeldt | |
| 2002/0113652 A1 | 8/2002 | Uto et al. | |
| 2002/0156513 A1 | 10/2002 | Borkan | |
| 2005/0246004 A1 | 11/2005 | Cameron et al. | |
| 2008/0146894 A1 | 6/2008 | Bulkes et al. | |
| 2009/0212856 A1 | 8/2009 | Chen et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2013/0289665 A1 | 10/2013 | Marnfeldt et al. | |
| 2014/0194772 A1 | 7/2014 | Single et al. | |
| 2014/0236042 A1 | 8/2014 | Parker et al. | |
| 2014/0296737 A1 | 10/2014 | Parker et al. | |
| 2015/0080982 A1 | 3/2015 | Funderburk | |
| 2015/0157861 A1 | 6/2015 | Aghassian | |
| 2015/0223710 A1 | 8/2015 | Cong et al. | |
| 2015/0231402 A1 | 8/2015 | Aghassian | |
| 2015/0282725 A1 | 10/2015 | Single | |
| 2015/0313487 A1 | 11/2015 | Single et al. | |
| 2015/0360038 A1 | 12/2015 | Zottola et al. | |
| 2016/0166164 A1 | 6/2016 | Obradovic et al. | |
| 2016/0287126 A1 | 10/2016 | Parker et al. | |
| 2016/0287182 A1 | 10/2016 | Single | |
| 2017/0042482 A1 | 2/2017 | Gunderson et al. | |
| 2017/0049345 A1 | 2/2017 | Single | |
| 2017/0071490 A1 | 3/2017 | Parker et al. | |
| 2017/0135624 A1 | 5/2017 | Parker | |
| 2017/0216587 A1 | 8/2017 | Parker | |
| 2017/0296823 A1 | 10/2017 | Hershey et al. | |
| 2017/0361101 A1 | 12/2017 | Single | |
| 2018/0071520 A1 | 3/2018 | Weerakoon et al. | |
| 2018/0071527 A1 | 3/2018 | Feldman et al. | |
| 2018/0110987 A1 | 4/2018 | Parker | |
| 2018/0117335 A1 | 5/2018 | Parker et al. | |
| 2018/0132747 A1 | 5/2018 | Parker et al. | |
| 2018/0132760 A1 | 5/2018 | Parker | |
| 2018/0133459 A1 | 5/2018 | Parker et al. | |
| 2018/0140831 A1 | 5/2018 | Feldman et al. | |
| 2018/0228391 A1 | 8/2018 | Parker et al. | |
| 2018/0228547 A1 | 8/2018 | Parker et al. | |
| 2018/0256052 A1 | 9/2018 | Parker et al. | |
| 2019/0076645 A1 | 3/2019 | Bower et al. | |
| 2019/0099602 A1 | 4/2019 | Esteller et al. | |
| 2019/0175915 A1 | 6/2019 | Brill et al. | |
| 2019/0209844 A1 | 7/2019 | Esteller et al. | |
| 2019/0275331 A1 | 9/2019 | Zhu | |
| 2019/0290900 A1 | 9/2019 | Esteller et al. | |
| 2019/0299006 A1 | 10/2019 | Marnfeldt | |
| 2019/0307341 A1 | 10/2019 | Parker et al. | |
| 2019/0366094 A1 | 12/2019 | Esteller et al. | |
| 2020/0155019 A1 | 5/2020 | Esteller et al. | |
| 2020/0305744 A1* | 10/2020 | Weerakoon | A61B 5/686 |
| 2020/0305745 A1* | 10/2020 | Wagenbach | A61B 5/686 |
| 2021/0236829 A1 | 8/2021 | Zhang et al. | |
| 2022/0040486 A1 | 2/2022 | Moffitt | |

FOREIGN PATENT DOCUMENTS

| | | |
|---|---|---|
| WO | 2017/100866 | 6/2017 |
| WO | 2017/173493 | 10/2017 |
| WO | 2017/210352 | 12/2017 |
| WO | 2017/219096 | 12/2017 |
| WO | 2020/251899 | 12/2020 |
| WO | 2021/046120 | 3/2021 |

OTHER PUBLICATIONS

International Search Report and Written Opinion regarding corresponding PCT Application No. PCT/US2022/080672, mailed Mar. 15, 2023.

* cited by examiner

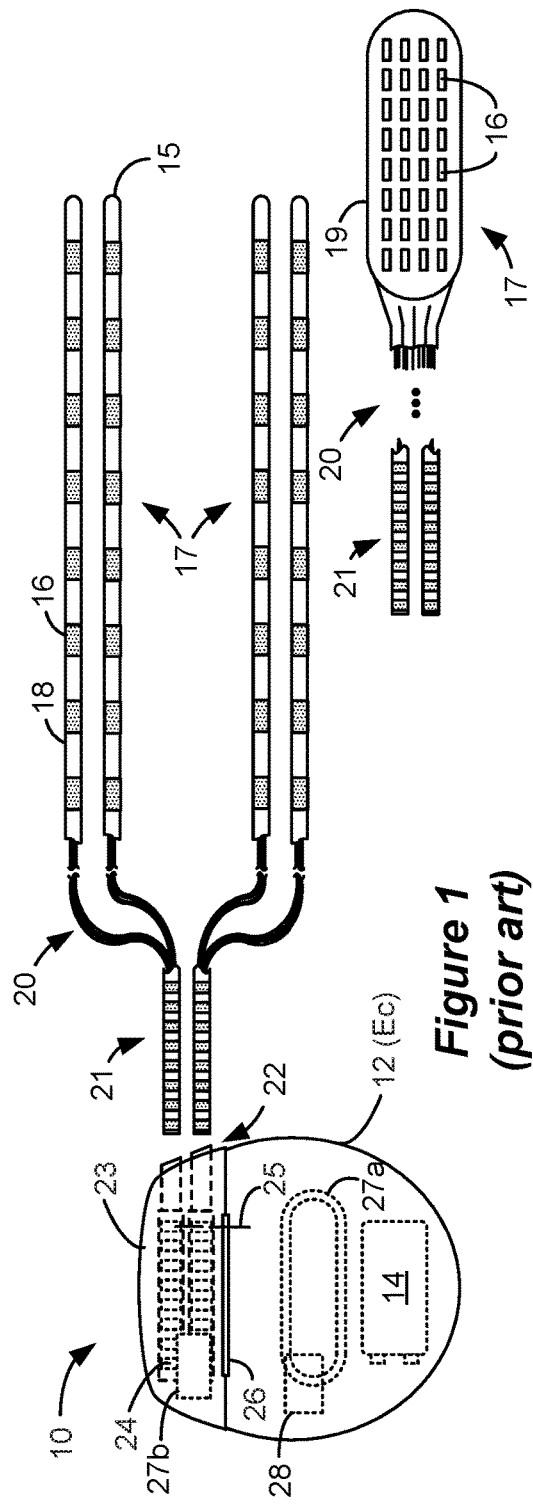
*Figure 1 (prior art)*
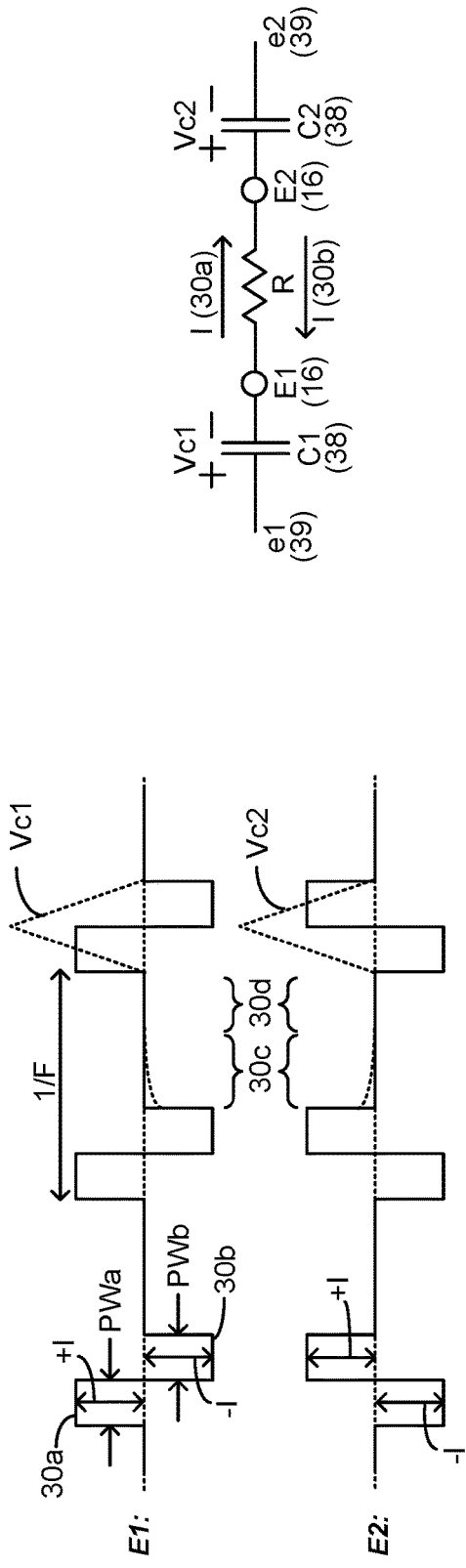
*Figure 2A (prior art)*
*Figure 2B (prior art)*

CIRCUITRY TO ASSIST WITH NEURAL SENSING IN AN IMPLANTABLE STIMULATOR DEVICE IN THE PRESENCE OF STIMULATION ARTIFACTS

CROSS REFERENCE TO RELATED APPLICATIONS

This is a non-provisional application of U.S. Provisional Patent Application Ser. No. 63/264,821, filed Dec. 2, 2021, which is incorporated herein by reference in its entirety, and to which priority is claimed.

FIELD OF THE INVENTION

This application relates to Implantable Medical Devices (IMDs), and more specifically to circuitry to assist with sensing neural responses to stimulation in an implantable stimulator device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) or Deep Brain Stimulation (DBS) system. However, the present invention may find applicability with any stimulator device system.

A stimulator system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12, or some conductive portion of the case, can also comprise an electrode (Ec). In an SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In a DBS application, the electrode leads are implanted in the brain through holes in the skull, and lead extension are used to connect the leads to the IPG which is typically implanted under the clavicle (collarbone). In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. SCS therapy can relieve symptoms such as chronic back pain, while DBS therapy can alleviate Parkinsonian symptoms such as tremor and rigidity. IPG 10 as described should be understood as including External Trial Stimulators (ETSs), which mimic operation of the IPG 10 during trials periods when leads have been implanted in the patient but the IPG 10 has not. See, e.g., U.S. Pat. No. 9,259,574 (disclosing an ETS).

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, WiFi, MICS, and the like.

Stimulation in IPG 10 is typically provided by pulses each of which may include a number of phases (30$i$), as shown in the example of FIG. 2A. Stimulation parameters typically include amplitude (current I, although a voltage amplitude V can also be used); frequency (F); pulse width (PW); the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during its first phase 30a), and thus provides pulses which source a positive current of amplitude +I to the tissue. Electrode E2 has been selected as a cathode (again during first phase 30a), and thus provides pulses which sink a corresponding negative current of amplitude −I from the tissue. This is an example of bipolar stimulation, in which the lead includes one anode pole and one cathode pole. Note that more than one electrode on the lead may be selected to act as an anode electrode to form an anode pole at a given time, and more than one electrode may be selected to act as a cathode to form a cathode pole at a given time, as explained further in U.S. Pat. No. 10,881,859. Stimulation provided by the IPG 10 can also be monopolar. In monopolar stimulation, the lead is programmed with a single pole of a given polarity (e.g., a cathode pole), with the conductive case electrode Ec acting as a return (e.g., an anode pole). Again, more than one electrode on the lead may be active to form the pole during monopolar stimulation.

IPG 10 as mentioned includes stimulation circuitry 28 to form prescribed stimulation at a patient's tissue. FIG. 3 shows an example of stimulation circuitry 28, which includes one or more current source circuits and one or more current sink circuits. The sources and sinks can comprise Digital-to-Analog converters (DACs), and may be referred to as PDACs and NDACs in accordance with the Positive (sourced, anodic) and Negative (sunk, cathodic) currents they respectively issue. In the example shown, a NDACi/PDACi pair is dedicated (hardwired) to a particular electrode node ei 39. Each electrode node ei 39 is associated with an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation as explained above. PDACs and NDACs can also comprise voltage sources.

Proper control of the PDACs and NDACs allows any of the electrodes 16 to act as anodes or cathodes to create a current through a patient's tissue, R, hopefully with good therapeutic effect. Consistent with the example provided in FIG. 2A, FIG. 3 shows operation during the first phase 30a in which electrode E1 has been selected as an anode electrode to source current I to the tissue R and E2 has been selected as a cathode electrode to sink current from the tissue. Thus PDAC1 and NDAC2 are digitally programmed to produce the desired current, I, with the correct timing (e.g., in accordance with the prescribed frequency and pulse widths). As mentioned above, more than one anode electrode and more than one cathode electrode may be selected at one time, and thus current can flow through the tissue R between two or more of the electrodes 16. Other stimulation circuitries 28 can also be used in the IPG 10, including ones that includes switching matrices between the electrode nodes ei 39 and the N/PDACs. See, e.g., 6,181,969, 8,606,362, 8,620,436, 11,040,192, and 10,912,942. Much of the stimulation circuitry 28 of FIG. 3, including the PDACs and NDACs, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as IPG master control circuitry 102 (see FIG. 5), telemetry circuitry (for interfacing off chip with telemetry antennas 27a and/or 27b), circuitry for generating the compliance voltage VH (as explained next), various measurement circuits, etc.

Power for the stimulation circuitry 28 is provided by a compliance voltage VH, as described in further detail in U.S. Patent Application Publications 2013/0289665 and 2018/0071520. The compliance voltage VH may be coupled to the source circuitry (e.g., the PDAC(s)), while ground may be coupled to the sink circuitry (e.g., the NDAC(s)), such that the stimulation circuitry 28 is powered by VH and ground. Other power supply voltages may be used with the PDACs and NDACs, and explained in U.S. Patent Application Publication 2018/0071520, but these aren't shown in FIG. 3 for simplicity.

Preferably, and as described in U.S. Pat. No. 11,040,202, the compliance voltage VH can be produced by a VH regulator 49. VH regulator 49 receives the voltage of the battery 14 (Vbat) and boost this voltage to a higher value required for the compliance voltage VH. VH regulator 49 can comprise an inductor-based boost converter or a capacitor-based charge pump for example. The regulator 49 can vary the value of VH based on measurements taken from the stimulation circuitry 28. As explained in detail in the '202 patent, VH measurement circuitry 51 can be used to measure the voltage drops across the active DACs (e.g., PDAC1 (Vp1) and NDAC2 (Vn2) in the example shown in FIG. 3) in the stimulation circuitry 28. Using such measurements allows VH to be established at an energy-efficient level: high enough to form the prescribed current without loading (i.e., without producing less current that prescribed), yet low enough to not needlessly waste power in the stimulation circuitry 28 when forming the prescribed current. In this respect, VH can be variable, and typically ranges from about 5 to 15 Volts.

The VH measurement circuitry 51 can output an enable signal VH(en1) indicating when VH regulator 49 should increase the level of VH, i.e., when the voltage drops across the active DACs are too low. This enable signal VH(en1) may be processed at logic 53 in conjunction with other signals explained below to determine a master enable signal VH(en) for the VH regulator 49. Logic 53 may be associated with the IPG's control circuitry 102. Master enable signal VH(en) when asserted causes the VH regulator 49 to increase VH (e.g., when the current starts to load). Deasserting VH(en) disable the VH regulator, which allows VH to naturally decrease over time until it needs to be increased again. This feedback generally causes VH to be established at an energy-efficient value appropriate for the current that is being provided by the stimulation circuitry 28.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861. While useful, DC-blocking capacitors 38 are not strictly required in all IPG designs and applications.

Referring again to FIG. 2A, the stimulation pulses as shown are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30a, charge will (primarily) build up across the DC-blockings capacitors C1 and C2 associated with the electrodes E1 and E2 used to produce the current, giving rise to voltages Vc1 and Vc2 (I=C*dV/dt). During the second pulse phase 30b, when the polarity of the current I is reversed at the selected electrodes E1 and E2, the stored charge on capacitors C1 and C2 is recovered, and thus voltages Vc1 and Vc2 hopefully return to 0V at the end the second pulse phase 30b.

Charge recovery using phases 30a and 30b is said to be "active" because the P/NDACs in stimulation circuitry 28 actively drive a current, in particular during the last phase 30b to recover charge stored after the first phase 30a. However, such active charge recovery may not be perfect, and some residual charge may be present in capacitive structures even after phase 30b is completed. Accordingly, the stimulation circuitry 28 can also provide for passive charge recovery. Passive charge recovery is implemented using passive charge recovery switches PRi 41 as shown in FIG. 3. These switches 41 when selected via assertion of control signals <Xi>couple each electrode node ei to a passive recovery voltage Vpr established on bus 43. As explained in U.S. Pat Nos. 10,716,937 and 10,792,491, this allows any stored charge to be recovered through the patient's tissue, R. Control signals <Xi> are usually asserted to cause passive charge recovery after each pulse (e.g., after each last phase 30b) during periods 30c shown in FIG. 2A. Because passive charge recovery involves capacitive discharge through the resistance R of the patient's tissue, such discharge manifests as an exponential decay in current, as shown in FIG. 2A. As also discussed in the '937 patent, each of the passive charge recovery switches 41 can be associated with a variable resistance, and as such each switch 41 can be controlled by a bus of signals <Xi> to control the resistance at which passive charge recovery occurs—i.e., the on resistance of the switches 41 when they are closed. Passive charge recovery during period 30c may be followed by a quiet period 30d during which no active current is driven by the DAC circuitry, and none of the passive recovery switches 41 are closed. This quiet period 30d may last until the next pulse is actively produced (e.g., phase 30a). Like the particulars of pulse phases 30a and 30b, the occurrence of passive charge recovery (30c) and any quiet periods (30d) can be prescribed as part of the stimulation program.

FIG. 4 shows various external systems 60, 70, and 80 that can wirelessly communicate data with the IPG 10. Such systems can be used to wirelessly transmit a stimulation program to the IPG 10—that is, to program its stimulation circuitry 28 to produce stimulation with desired amplitudes and timings as described earlier. Such systems may also be used to adjust one or more stimulation parameters of a stimulation program that the IPG 10 is currently executing, and/or to wirelessly receive information from the IPG 10, such as various status information, etc.

External controller 60 can be as described in U.S. Patent Application Publication 2015/0080982 for example, and may comprise a portable, hand-held controller dedicated to work with the IPG 10. External controller 60 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. External controller 60 includes a display 61 and a means for entering commands, such as buttons 62 or selectable graphical icons provided on the display 61. The external controller 60's user interface enables a patient to adjust stimulation parameters, although it may have limited functionality when compared to systems 70 and 80, described shortly. The external controller 60 can have one or more antennas capable of communicating with the IPG 10. For example, the external controller 60 can have a near-field magnetic-induction coil antenna 64a capable of wirelessly communicating with the coil antenna 27a in the IPG 10. The external controller 60 can also have a far-field RF antenna 64b capable of wirelessly communicating with the RF antenna 27b in the IPG 10.

Clinician programmer 70 is described further in U.S. Patent Application Publication 2015/0360038, and can comprise a computing device such as a desktop, laptop, or notebook computer, a tablet, a mobile smart phone, a Personal Data Assistant (PDA)-type mobile computing device, etc. In FIG. 4, the computing device is shown as a laptop computer that includes typical computer user interface means such as a display 71, buttons 72, as well as other user-interface devices such as a mouse, a keyboard, speakers, a stylus, a printer, etc., not all of which are shown for convenience. Also shown in FIG. 4 are accessory devices for the clinician programmer 70 that are usually specific to its operation as a stimulation controller, such as a communication "wand" 76 coupleable to suitable ports on the computing device. The antenna used in the clinician programmer 70 to communicate with the IPG 10 can depend on the type of antennas included in the IPG 10. If the patient's IPG 10 includes a coil antenna 27a, wand 76 can likewise include a coil antenna 74a to establish near-field magnetic-induction communications at small distances. In this instance, the wand 76 may be affixed in close proximity to the patient, such as by placing the wand 76 in a belt or holster wearable by the patient and proximate to the patient's IPG 10. If the IPG 10 includes an RF antenna 27b, the wand 76, the computing device, or both, can likewise include an RF antenna 74b to establish communication with the IPG 10 at larger distances. The clinician programmer 70 can also communicate with other devices and networks, such as the Internet, either wirelessly or via a wired link provided at an Ethernet or network port.

External system 80 comprises another means of communicating with and controlling the IPG 10 via a network 85 which can include the Internet. The network 85 can include a server 86 programmed with communication and control functionality, and may include other communication networks or links such as WiFi, cellular or land-line phone links, etc. The network 85 ultimately connects to an intermediary device 82 having antennas suitable for communication with the IPG's antenna, such as a near-field magnetic-induction coil antenna 84a and/or a far-field RF antenna 84b. Intermediary device 82 may be located generally proximate to the IPG 10. Network 85 can be accessed by any user terminal 87, which typically comprises a computer device associated with a display 88. External system 80 allows a remote user at terminal 87 to communicate with and control the IPG 10 via the intermediary device 82.

FIG. 4 also shows circuitry 90 involved in any of external systems 60, 70, or 80. Such circuitry can include control circuitry 92, which can comprise any number of devices such as one or more microprocessors, microcomputers, FPGAs, DSPs, other digital logic structures, etc., which are capable of executing programs in a computing device. Such control circuitry 92 may contain or coupled with memory 94 which can store external system software 96 for controlling and communicating with the IPG 10, and for rendering a Graphical User Interface (GUI) 99 on a display (61, 71, 88) associated with the external system. In external system 80, the external system software 96 would likely reside in the server 86, while the control circuitry 92 could be present in either or both the server 86 or the terminal 87.

SUMMARY

In a first example, a stimulator device is disclosed which may comprise: a plurality of electrode nodes, wherein each of the electrode nodes is associated with a different electrode configured to contact a patient's tissue, wherein at least one of the electrodes comprises a sensing electrode to receive a voltage from the tissue, wherein each electrode node associated with the at least one sensing electrode comprises a sensing electrode node; sense amplifier circuitry comprising a first amplifier with a first input and a first output and a second amplifier with a second input and a second output; and monitoring circuitry configured to assess a voltage at each sensing electrode node, wherein the monitoring circuitry is configured based on the assessed one or more voltages to select use of the first or the second amplifier to determine a signal in the tissue.

In one example, the device may further comprise input switching circuitry between each sensing electrode node and the first input and between each sensing electrode node and the second input, wherein the monitoring circuitry is configured to select the first or the second amplifier by controlling the input switching circuitry to either connect each sensing electrode node to the first input or to the second input. In one example, the device may further comprise an analog-to-digital converter (ADC), wherein the ADC is configured to provide a digitized representation of the determined signal; and output switching circuitry between the first output and the ADC and between the second output and the ADC, wherein the monitoring circuitry is configured to select the first or the second amplifier by controlling the output switching circuitry to either couple the first output to communicate with the ADC or to couple the first output to communicate with the ADC. In one example, the device may further comprise processing circuitry, wherein the coupled first or second output communicates with the ADC via the processing circuitry. In one example, the processing circuitry comprises an additional amplifier to impart a gain to the first or second output of the selected first or second amplifier. In one example, the processing circuitry comprises filter circuitry to filter the first or second output of the selected first or second amplifier. In one example, the first amplifier is powered by a first power supply voltage, and wherein the second amplifier is powered by a second power supply voltage higher than the first power supply voltage. In one example, the device may further comprise stimulation circuitry configured to provide stimulation to one or more of the electrode nodes to provide stimulation to the patient's tissue via associated stimulation electrodes. In one example, the stimulation electrodes are different from the at least one sensing electrode. In one example, the stimulation circuitry is powered by the second power supply voltage. In one example, the monitoring circuitry is configured to assess the voltage at each sensing electrode node by comparing the voltage at each sensing electrode node to a first voltage. In one example, the monitoring circuitry is configured to select the first amplifier if the voltage at each sensing electrode node is below the first voltage. In one example, the monitoring circuitry is configured to select the second amplifier if the voltage at any sensing electrode node is above the first voltage. In one example, the first amplifier is powered by a first power supply voltage, wherein the first voltage is set relative to the first power supply voltage. In one example, the first voltage equals the first power supply voltage. In one example, the monitoring circuitry is further configured upon the occurrence of an initialization event to select the use of the first amplifier during an initialization period. In one example, the monitoring circuitry is configured to select the use of the first or the second amplifier based on the assessed one or more voltages after the initialization period. In one example, the monitoring circuitry comprises an algorithm to assess the voltage at each sensing electrode node, wherein the algorithm is configured to generate a control signal based on the assessed voltages to select the use of the first or the second amplifier. In one example, the device further comprises a DC-blocking capacitance between each of the electrode nodes and its associated electrode. In one example, the first amplifier and the second amplifier comprise differential amplifiers, wherein the first input comprises a first differential input, and wherein the second input comprises a second differential input. In one example, two of the electrodes comprise the sensing electrodes to receive the voltage from the tissue, wherein two sensing electrode nodes are associated with the two sensing electrodes, wherein the monitoring circuitry is configured to assess the voltages at the two sensing electrode nodes, wherein the monitoring circuitry is configured based on the assessed voltages to select the use of the first or the second amplifier by respectively connecting the two sensing electrode nodes to the first differential input or the second differential input. In one example, only one of the electrodes comprises the sensing electrode to receive the voltage from the tissue, wherein one sensing electrode node is associated with the sensing electrode, wherein the monitoring circuitry is configured to assess the voltage at the one sensing electrode node, wherein the monitoring circuitry is configured based on the assessed voltage to select the use of the first or the second amplifier by respectively connecting the sensing electrode node to the first differential input or the second differential input, wherein the sensing electrode node is compared to a reference voltage of the selected first or second amplifier.

In a second example, a stimulator device is disclosed which may comprise: a plurality of electrode nodes, wherein each of the electrode nodes is associated with a different electrode configured to contact a patient's tissue, wherein at least one of the electrodes comprises a sensing electrode to receive a voltage from the tissue, wherein each electrode node associated with the at least one sensing electrode comprises a sensing electrode node; sense amplifier circuitry comprising a first amplifier with a first input and a first output and a second amplifier with a second input and a second output; and input switching circuitry controllable to connect each sensing electrode node to either the first input to enable the first amplifier to determine a signal in the tissue, or to the second input to enable the second amplifier to determine the signal in the tissue.

In one example, the device may further comprise monitoring circuitry configured to assess a voltage at each sensing electrode node, wherein the monitoring circuitry is configured based on the assessed one or more voltages to control the input switching circuitry. In one example, the device may further comprise an analog-to-digital converter (ADC), wherein the ADC is configured to provide a digitized representation of the determined signal; and output switching circuitry controllable to either couple the first output to communicate with the ADC or to couple the first output to communicate with the ADC. In one example, the monitoring circuitry is configured based on the assessed one or more voltages to control the output switching circuitry. In one example, the device may further comprise processing circuitry, wherein the coupled first or second output communicates with the ADC via the processing circuitry. In one example, the processing circuitry comprises an additional amplifier to impart a gain to the first or second output coupled to communicate with the ADC. In one example, the processing circuitry comprises filter circuitry to filter the first or second output coupled to communicate with the ADC. In one example, the first amplifier is powered by a first power supply voltage, and wherein the second amplifier is powered by a second power supply voltage higher than the first power supply voltage. In one example, the device may further comprise stimulation circuitry configured to provide stimulation to one or more of the electrode nodes to provide stimulation to the patient's tissue via associated stimulation electrodes. In one example, the stimulation electrodes are different from the at least one sensing electrode. In one example, the stimulation circuitry is powered by the second power supply voltage. In one example, the monitoring circuitry is configured to assess the voltage at each sensing electrode node by comparing the voltage at each sensing electrode node to a first voltage. In one example, the monitoring circuitry is configured to control the input switching circuitry to connect each sensing electrode nodes to the first input if the voltage at each sensing electrode node is below the first voltage. In one example, the monitoring circuitry is configured to control the input switching circuitry to connect each sensing electrode nodes to the second input if the voltage at any sensing electrode node is above the first voltage. In one example, the first amplifier is powered by a first power supply voltage, wherein the first voltage is set relative to the first power supply voltage. In one example, the first voltage equals the first power supply voltage. In one example, the monitoring circuitry is further configured upon the occurrence of an initialization event to control the input switching circuitry to connect each sensing electrode node to the first input during an initialization period. In one example, the monitoring circuitry is further configured to control the input switching circuitry to connect each sensing electrode nodes to either the first input or the second input based on the assessed one or more voltages after the initialization period. In one example, the monitoring circuitry comprises an algorithm to assess the voltage at each sensing electrode node, wherein the algorithm is configured to generate a control signal based on the assessed voltages to control the input switching circuitry. In one example, the device may further comprise a DC-blocking capacitance between each of the electrode nodes and its associated electrode. In one example, the first amplifier and the second amplifier comprise differential amplifiers, wherein the first input comprises a first differential input, and wherein the second input comprises a second differential input. In one example, two of the electrodes comprise the sensing electrodes to receive the voltage from the tissue, wherein two sensing electrode nodes are associated with the two sensing electrodes, wherein the input switching circuitry is controllable to connect the two sensing electrode nodes to either the first differential input to enable the first amplifier to determine the signal as a difference between signals at the two sensing electrode nodes, or to the second differential input to enable the second amplifier to determine the signal as a difference between the signals at the two sensing electrode nodes. In one example, only one of the electrodes comprises the sensing electrode to receive the voltage from the tissue, wherein one sensing electrode node is associated with the sensing electrode, wherein the input switching circuitry is controllable to connect the sensing electrode node to either the first differential input to enable the first amplifier to determine the signal as a difference between a signal at the sensing electrode node and a reference voltage, or to the second differential input to enable the second amplifier to determine the signal as a difference between a signal at the sensing electrode node and a reference voltage.

In a third example, a stimulator device is disclosed which may comprise: a plurality of electrode nodes, wherein each of the electrode nodes is associated with a different electrode configured to contact a patient's tissue; a DC-blocking capacitor between each of the electrode nodes and its associated electrode; wherein at least one of the electrodes comprises a sensing electrode to receive a voltage from the tissue, wherein each electrode node associated with the at least one sensing electrode comprises a sensing electrode node; sense amplifier circuitry comprising a first input connected to one of the at least one sensing electrodes and a second input, the sense amplifier circuitry further comprising a differential output comprising a first output and a second output; and DC offset compensation circuitry configured to receive the first and second output, and to produce a DC current, wherein a magnitude of the DC current is a function of a difference of voltages at the first and second outputs, wherein the DC current is provided to the first input to adjust a DC voltage at the first input equal to a DC voltage at the second input.

In one example, the current adjusts the DC voltage at the first input by charging or discharging the DC-blocking capacitor associated with the first input. In one example, the current can be positive or negative. In one example, the DC voltage at the second input comprises a constant reference voltage. In one example, the second input is connected to another one of the at least one sensing electrodes. In one example, the DC offset compensation circuitry is configured to convert the voltages at the first and second output to respective first and second currents. In one example, the magnitude of the DC current is a function of a difference of the first current and the second current. In one example, the differential output is indicative of a signal sensed in the tissue. In one example, the device may further comprise an analog-to-digital converter (ADC), wherein the ADC is configured to provide a digitized representation of the differential output. In one example, the device may further comprise stimulation circuitry configured to provide stimulation to one or more of the electrode nodes to provide stimulation to the patient's tissue via associated stimulation electrodes. In one example, the stimulation electrodes are different from the at least one sensing electrode. In one example, the stimulation circuitry is powered by a power supply voltage. In one example, the sense amplifier circuitry is powered by the power supply voltage. In one example, the device may further comprise monitoring circuitry configured to assess a voltage at at least the first input. In one example, the monitoring circuitry is further configured to assess a voltage at the second input. In one example, the DC offset compensation circuitry is further configured to receive gain control signals to impart a gain to the magnitude of the DC current.

BRIEF DESCRIPTION OF THE DRAWINGS

FIG. 1 shows an Implantable Pulse Generator (IPG), in accordance with the prior art.

FIGS. 2A and 2B show an example of stimulation pulses producible by the IPG, in accordance with the prior art.

DETAILED DESCRIPTION

An increasingly interesting development in pulse generator systems is the addition of sensing capability to complement the stimulation that such systems provide. For example, and as explained in U.S. Patent Application Publication 2017/0296823, it can be beneficial to sense a neural response produced by neural tissue that has received stimulation from an IPG. U.S. Patent Application Publication 2017/0296823 shows an example where sensing of neural responses is useful in an SCS context, and in particular discusses the sensing of Evoked Compound Action Potentials, or "ECAPs." U.S. Patent Application Publication 2022/0040486 shows an example where sensing of neural responses is useful in a DBS context, and in particular discusses the sensing of Evoked Resonant Neural Activity, or "ERNA."

Figure 5:
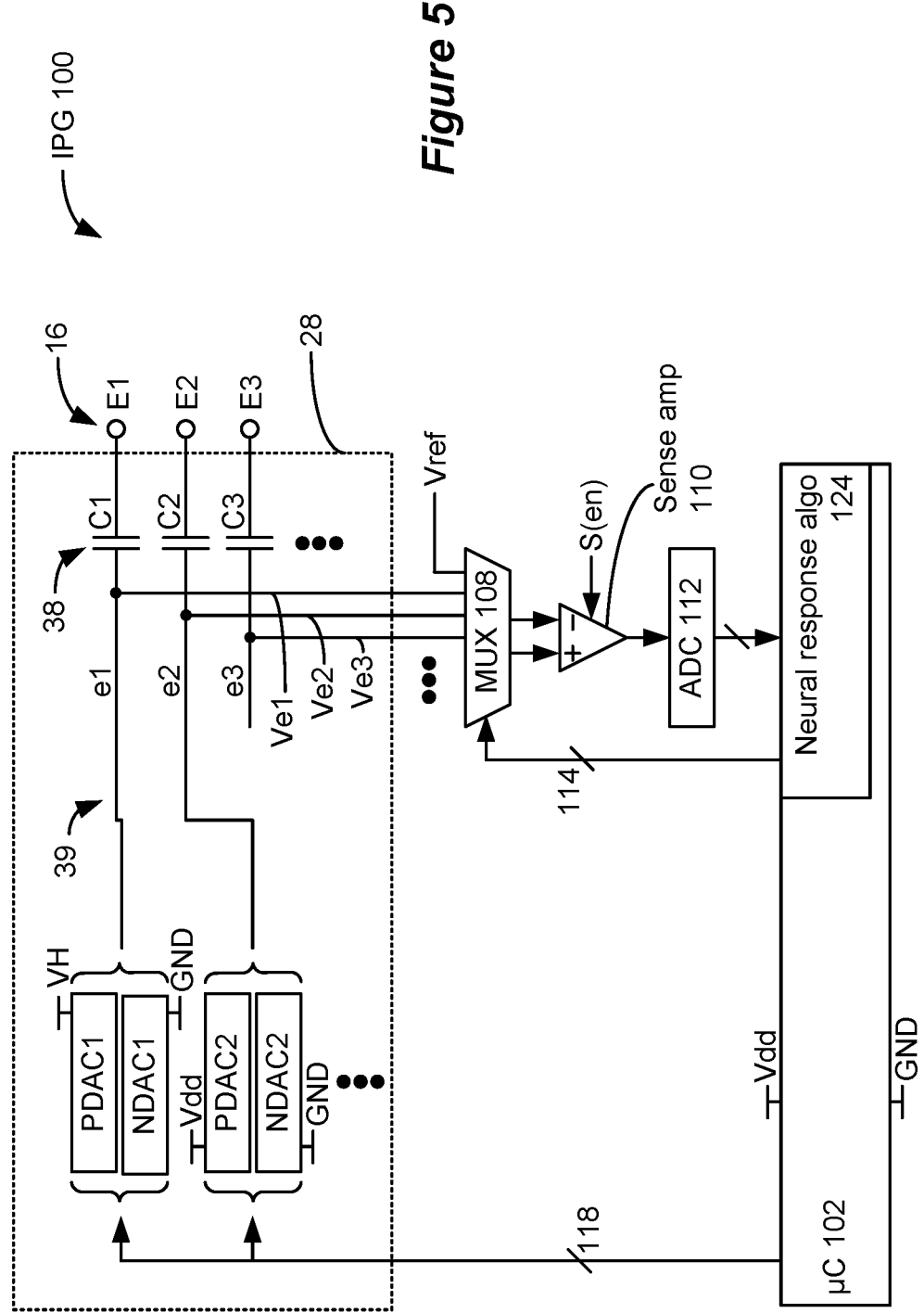
FIG. 5 shows an IPG having neural response sensing capability.

FIG. 5 shows basic circuitry for sensing neural responses in an IPG 100. The IPG 100 includes control circuitry 102, which may comprise a microcontroller for example, such as Part Number MSP430, manufactured by Texas Instruments, which is described in data sheets accessible on the Internet. Other types of control circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs) in the IPG 10 as described earlier, which ASIC(s) may additionally include the other circuitry shown in FIG. 5.

FIG. 5 includes the stimulation circuitry 28 described earlier (FIG. 3), including one or more DACs (PDACs and NDACs). A bus 118 provides digital control signals to the DACs to produce currents or voltages of prescribed amplitudes and with the correct timing at the electrodes selected for stimulation. The electrode current paths to the electrodes 16 include the DC-blocking capacitors 38 described earlier.

Figure 4:
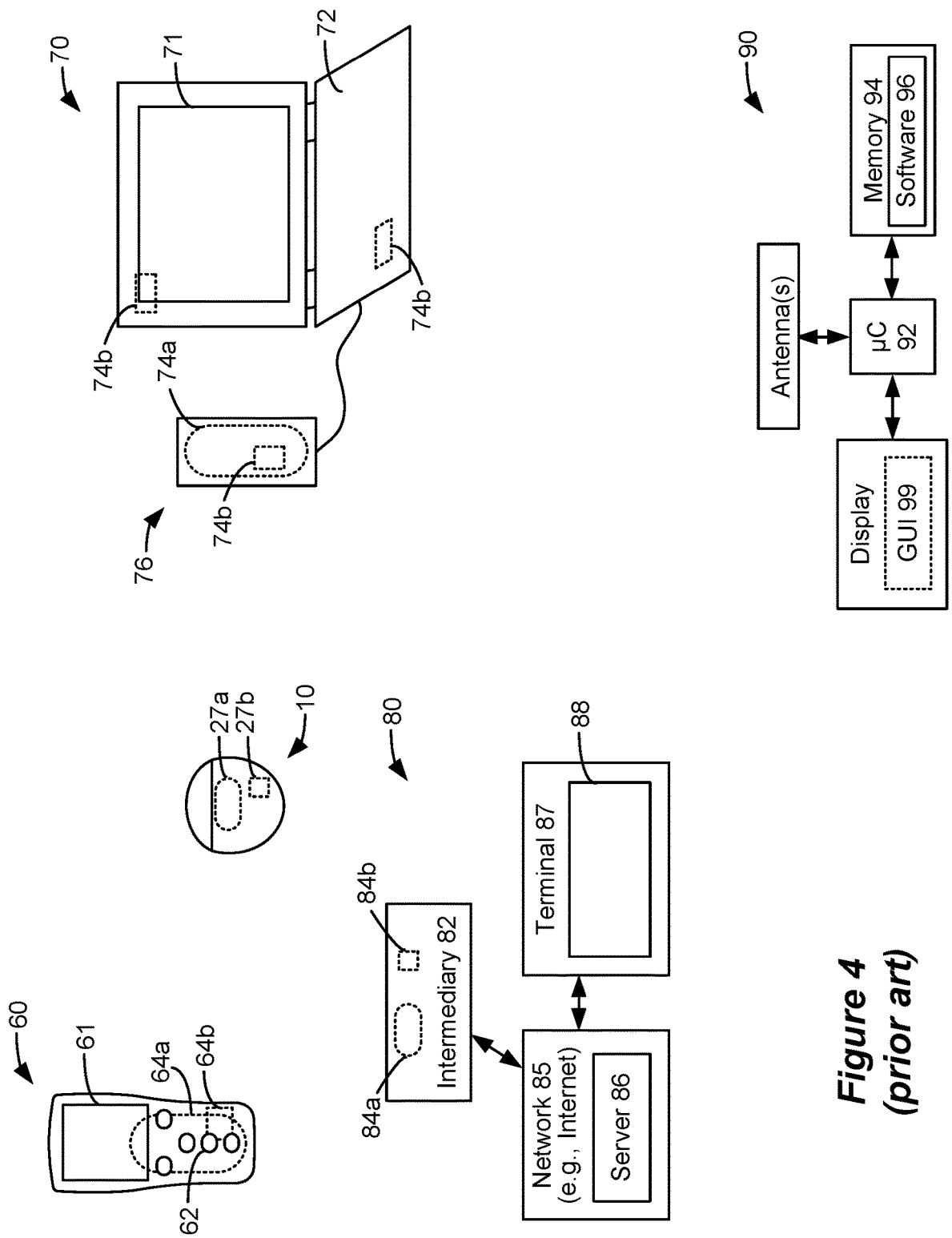
FIG. 4 shows various external devices capable of communicating with and programming stimulation in an IPG, in accordance with the prior art.

FIG. 5 also shows circuitry used to sense neural responses. As shown, the electrode nodes 39 are input to a multiplexer (MUX) 108. The MUX 108 is controlled by a bus 114, which operates to select one or more electrode nodes, and hence to designate corresponding electrodes 16 as sensing electrodes. The sensing electrode(s) selected via bus 114 can be determined automatically by control circuitry 102 and/or a neural response algorithm 124, as described further below. However, the sensing electrode(s) may also be selected by the user (e.g., a clinician) via an external system 60, 70 or 80 (FIG. 4).

Figure 6:
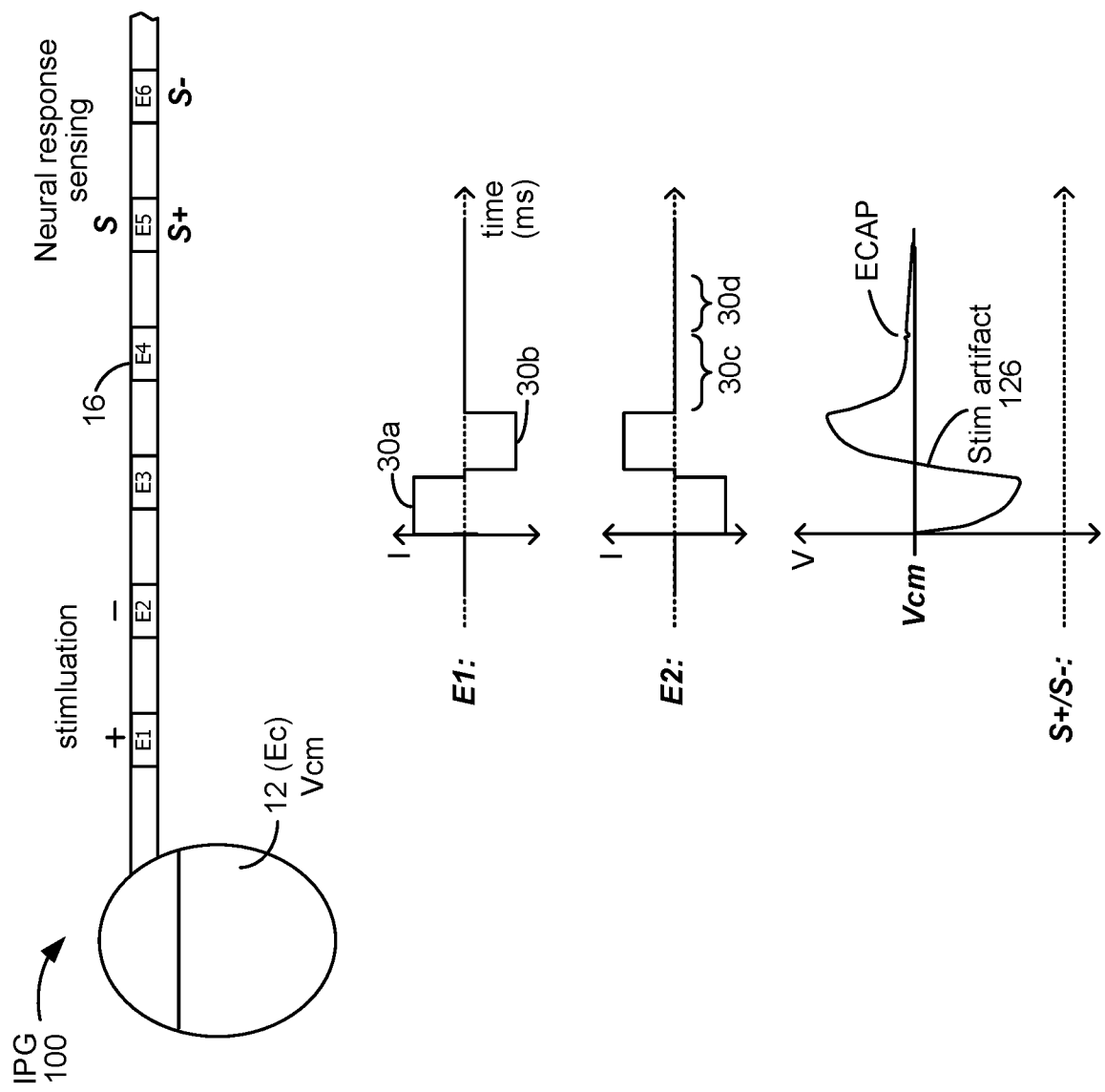
FIG. 6 shows stimulation producing a neural response, and the sensing of that neural response at at least one electrode of the IPG.

Electrodes selected as sensing electrodes are provided by the MUX 108 to a sense amplifier circuitry 110, and sensing can occur differentially using two sensing electrodes, or using a single sensing electrode. This is shown in the example of FIG. 6. If single-ended sensing is used, a single electrode (e.g., E5) is selected as a single sensing electrode (S) and is provided to the positive terminal of the sense amp circuitry 110, where it is compared to a reference voltage Vref provided to the negative input. The reference voltage Vref can comprise any DC voltage produced within the IPG, such as ground, the voltage of the battery (Vbat), or some fraction of the compliance voltage VH (such as VH/2). If differential sensing is used, two electrodes (e.g., E5 and E6) are selected as sensing electrodes (S+ and S−) by the MUX 108, with one electrode (e.g., E5) provided to the positive terminal of the sense amp circuitry 110, and the other (e.g., E6) provided to the negative terminal. Differential sensing can be useful to cancel any common mode voltages present in the tissue and reflected at the electrodes, such as voltages created by the stimulation itself. See, e.g., U.S. Patent Application Publication 2021/0236829. Although only one sense amp circuit 110 is shown in FIG. 5 for simplicity, there could be more than one, such as a sense amp dedicated to each electrode node. In this case, MUX 108 would not be necessary, and each sense amp could be activated as needed depending on which electrodes are selected as sensing electrodes. The timing at which sensing occurs can be affected by a sensing enable signal S(en), as discussed further below. Further details of sense amp circuitry 110 are discussed later with reference to FIG. 7.

The analog waveform comprising the sensed neural response and output by the sense amp circuitry 110 is preferably converted to digital signals by an Analog-to-Digital converter (ADC) 112, and input to the IPG's control circuitry 102. The ADC 112 can be included within the control circuitry 102's input stage as well. The control circuitry 102 can be programmed with a neural response algorithm 124 to evaluate the neural responses, and to take appropriate actions as a result. For example, the neural response algorithm 124 may change the stimulation in accordance with the sensed neural response, and can issue new control signals via bus 118 to change operation of the stimulation circuitry 28 to affect better treatment for the patient. The neural response algorithm 124 may also cause the selection of new sensing electrode(s), which can be affected by issuing new control signals on bus 114. Selecting optimal sensing electrode(s) can be important, and may be determined in light of stimulation that is being provided. In this regard, sensing electrodes may be selected near enough to the electrodes providing stimulation (e.g., E1 and E2) to allow for proper neural response sensing, but far enough from the stimulation that the stimulation doesn't substantially interfere with neural response sensing. See, e.g., U.S. Patent Application Publication 2020/0155019.

Neural responses to stimulation are typically small-amplitude AC signals on the order of microVolts or milliVolts, which can make sensing difficult. The sense amp circuitry 110 needs to be capable of resolving this small signal, and this is particularly difficult when one realizes that this small signal typically rides on a background voltage otherwise present in the tissue. As explained in U.S. Patent Application Publication 2020/0305744, which is incorporated by reference in its entirety, this background voltage can be caused by the stimulation itself. This is shown in the waveforms at the bottom of FIG. 6, which shows the current stimulation pulses, and the signals received at selected sensing electrodes S+ or S−. The sensed signal from the tissue at the sensing electrode(s) includes a neural response—in this case an ECAP—and may also include a stimulation artifact 126 which results from the electromagnetic field that forms in the tissue as a result of the stimulation. The neural response (e.g., ECAP) may be present during active stimulation (e.g., during phases 30a or 30b) when the stimulation artifact is higher and perhaps varying more significantly, or after active stimulation (as shown in FIG. 6) when the stimulation artifact is lower (e.g., during passive charge recovery or quiet periods 30d). Because the DAC circuitry used to provide the stimulation is powered by power supply voltages VH and ground (see FIG. 3), the stimulation artifact 126 will vary between these voltages, and can comprise several Volts.

Differential sensing is useful because it allows the sense amp circuitry 110 to subtract any common mode voltages like the stimulation artifact 126 present in the tissue, hence making the neural response easier to resolve. However, this will not remove the stimulation artifact 126 completely, because the stimulation artifact 126 will not be exactly the same at each sensing electrode. Therefore, even when using differential sensing, it may be difficult to resolve the small signal neural response which may still ride on a significant background voltage.

That being said, the stimulation artifact 126 is not always a detriment to sensing. In fact, sometimes it is useful to sense stimulation artifacts 126 in their own right, because like neural responses they can also provide information relevant to adjusting a patient's stimulation, or to automatically selecting a best combination of sensing electrodes. See, e.g., U.S. Patent Application Publications 2020/251899 and 2021/0236829.

U.S. Pat. No. 11,040,202, which is incorporated herein by reference in its entirety, describes circuitry that assists in neural sensing by holding the tissue via a capacitor (such as the DC-blocking caps 38) to a common mode voltage, Vcm. This common mode voltage Vcm is preferably established at the conductive case electrode Ec as shown in FIG. 6, although another lead-based electrode could also be used to provide Vcm. See, e.g., U.S. Patent Application Publication No. 2023/0138443. As these references disclose, it is beneficial to establish Vcm with reference to the power supply voltage of the DAC circuitry—i.e., the compliance voltage VH explained earlier—because the voltages in the tissue will be between this voltage and ground. Most preferably, Vcm can equal approximately VH/2. In any event, when a common mode voltage Vcm is provided to the tissue, AC signals present in the tissue (neural responses, any stimulation artifacts) will also be referenced to this voltage. This is a helpful improvement, because it tends to stabilize the DC level of the signals being input to the sense amp circuitry 110 by the sensing electrodes.

But such circuitry doesn't address that at certain times AC signals being sensed (in particular the situation artifacts 126) may be too large for the sense amplifier circuitry 110 to reliably handle. In this regard, note that a typical sense amp circuit will include (as explained further below) a differential amplifier ("diff amp"). Generally, the diff amp only works reliably if the signals at its inputs (i.e., the sensing electrode(s)) do not exceed the power supply voltage used to power the diff amp; if the inputs are higher than the power supply voltage, the output of the diff amp will saturate.

The IPG 100 typically provides an internal power supply voltage Vdd. This power supply voltage Vdd typically powers the bulk of the circuitry in the IPG 100, such as the control circuitry 102 (see FIG. 5), and is typically generated (regulated) from the battery voltage Vbat. Vdd is typically a low voltage, such as 3.3 Volts. The diff amp in the sense amp circuitry 110 could be powered with this voltage Vdd, but this has benefits and drawbacks. A low-voltage diff amp made with smaller low-voltage components would generally be less noisy, thus making it easier to resolve the small neural response signals. However, a low-voltage diff amp would not be able to resolve neural responses if they are riding on a tissue voltage greater than Vdd. As discussed above, the stimulation artifact 126 (produced as a function of the larger compliance voltage VH) can comprise several Volts. Therefore, the signal at a given sensing electrode may be higher than Vdd, making sensing of the neural response impossible when a low-voltage diff amp is used. This is further unfortunate, because as mentioned above it can sometimes be useful to sense the stimulation artifact 126 in its own right.

Figure 3:
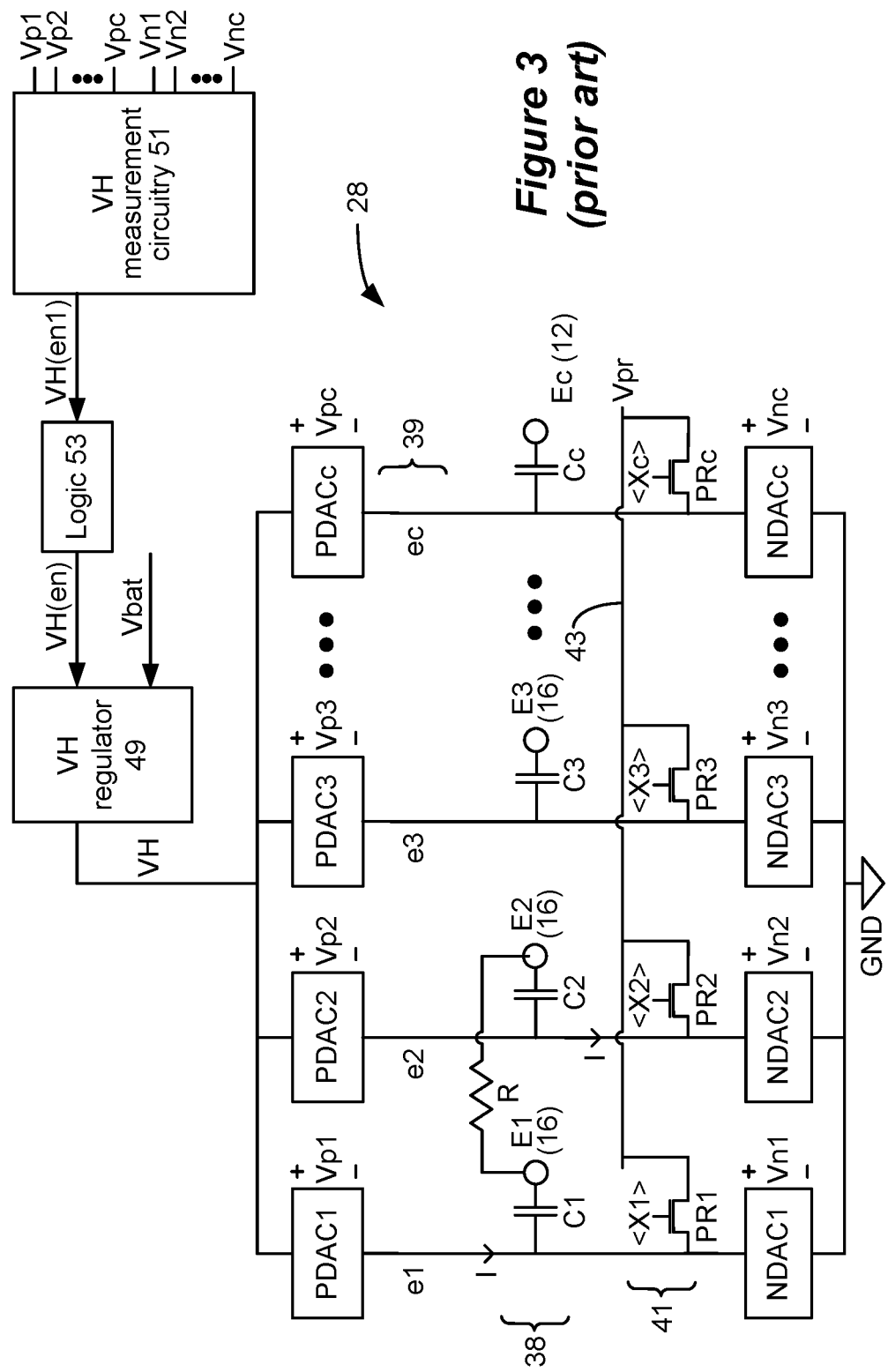
FIG. 3 shows stimulation circuitry useable in the IPG, in accordance with the prior art.

Alternatively, the diff amp used in the sense amp circuitry 110 could be powered using the compliance voltage VH, which as described earlier can be used to power the DAC circuitry that produces the simulation currents (see FIG. 3). As noted earlier, this compliance voltage VH, although variable, is typically larger than Vdd. But again powering the diff amp using VH has benefits and drawbacks. Such a high-voltage diff amp would be made of larger, more robust high-voltage components that would generally be able to handle the voltages at its inputs. These inputs would typically be less than VH, and thus a high-voltage diff amp should be able to reliably sense without saturating. A high-voltage diff amp would also be able to resolve the stimulation artifact 126 itself, which as noted above can be useful to sense. However, a high-voltage diff amp would also be noisier than a low-voltage diff amp, potentially making the neural responses more difficult to resolve. Further, while a high-voltage diff amp can be designed to achieve a signal-to-noise ratio similar to that of a low-voltage diff amp, it will require more power consumption to do so.

Figure 7:
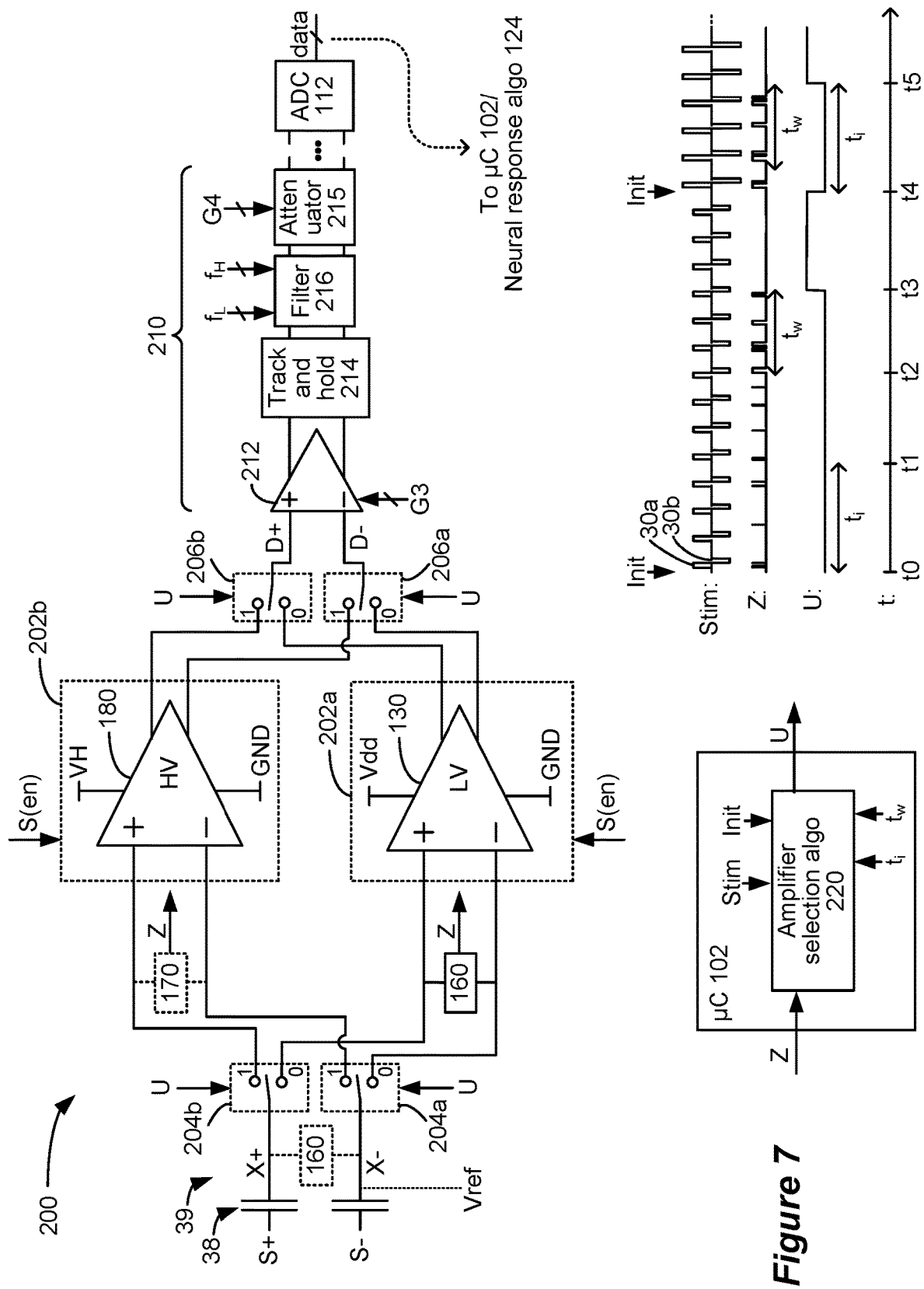
FIG. 7 shows sense amp circuitry useable in an IPG having sensing capability. The sense amp circuit includes a low-voltage sense amp circuit and a high voltage sense-amp circuit, either of which is selectable for use based on an assessment of the magnitude of at least one of the input signals.

To address this issue, the inventors disclose improved sense amp circuitry 200 for an IPG 100, which may be used in lieu of sense amp circuitry 110 as discussed earlier. An example of sense amp circuitry 200 is shown in FIG. 7, which is explained at a high level before delving into its specifics. Sense amp circuitry 200 comprises two sense amp circuits 202a and 202b. These sense amp circuits 202a and 202b are preferably different in design, and involve different circuitries, as described in detail below. Preferably, sense amp circuit 202a comprises a low-voltage diff amp 130, powered by Vdd. Sense amp circuit 202b by contrast comprises a high-voltage diff amp 180, powered by the compliance voltage VH.

Either of these sense amp circuitries 202a or 202b can be selected to sense a neural response at the selected sensing electrodes S+ and S−, and this selection is selected based on an assessment of the magnitude of either or both of the input signals X+ and X− at the electrode nodes 39 of the selected sensing electrodes S+ and S−. This assessment is made using monitoring circuitry 160, which issues a digital magnitude signal Z indicative of the magnitude of the input signals X+ and X−. Monitoring circuitry 160 is explained in detail later, but is briefly explained here. In the example shown, the monitoring circuitry 160 receives the inputs X+ and X− at the inputs to the low-voltage sense amp circuit 202a (i.e., after switches 204a and 204b). However, the monitoring circuitry 160 could alternatively or additionally assess X+ and X− directly at the electrode nodes 39, or at the inputs to the high-voltage sense amp circuit 202b (170, FIG. 10), as shown in dotted lines. (Optional monitoring circuitry 170 is discussed later with reference to FIG. 10). As explained further below, monitoring circuitry 160 sets magnitude signal Z to '0' if the inputs X+ and/or X− are of a suitable magnitude to be handled by the low-voltage diff amp 130. If the magnitude of either of these inputs X+ or X− is too high, monitoring circuitry 160 sets Z to '1'.

Information provided by the magnitude signal Z is ultimately used to select use of either the low-voltage sense amp circuit 202a or the high-voltage sense amp circuit 202b, although it is preferable to first process this signal. Specifically, and as shown in FIG. 7, the magnitude signal Z is provided to an amplifier selection algorithm 220, which determines a control signal U used to select use of one of the sense amp circuits 202a or 202b. Amplifier selection algorithm 220 may be programmed as firmware in the IPG 100's control circuitry 102, and is explained further below. Algorithm 220 may comprise a part of the monitoring circuitry 160, and the monitoring circuitry 160 can comprise a part of the control circuitry 102 or vice versa.

The selection of either of the sense amp circuits 202a or 202b using control signal U is facilitated by the use of switches 204a, 204b, 206a, and 206b, which operate to either connect or disconnect the differential inputs and outputs of the circuits 202a and 202b to or from the rest of the circuitry. In this example, it is assumed that U='0' selects use of the low-voltage sense amp circuit 202a. When U='0', switches 204a and 204b (together comprising input switching circuitry) connect the electrode nodes 39 (input X− and X+ respectively) at the sensing electrodes S− and S+ to the input of the low-voltage diff amp 130 in the low-voltage sense amp 202a. Further, when U='0', switches 206a and 206b (together comprising output switching circuitry) connect the output of the low-voltage diff amp 130 to analog outputs D− and D+ respectively, and ultimately to the ADC 112 to digitize the signal (e.g., neural response) sensed by the diff amp 130. Notice that the output (D+ and D−) may be processed further by optional analog processing circuitry 210 before being digitized at the ADC 112, and this circuitry 210 is explained further below. U='1' by contrast selects use of the high-voltage sense amp circuit 202a, which connects (via 204a and 204b) X− and X+ to the differential inputs of the high-voltage diff amp 180 in the high-voltage sense amp 202b, and which connects (via 206a and 206b) the differential outputs of the high-voltage diff amp 130 to the analog outputs D− and D+.

An example of the manner in which the amplifier selection algorithm 220 can operate is shown using the timing diagrams shown at the bottom of FIG. 7. Generally speaking, the algorithm 220 assesses the magnitude signal Z over a period of time to determine whether use of the low- or high-voltage sense amp circuit 202a or 202b is more appropriate. As shown, the amplifier selection algorithm 220 can receive certain programmed inputs to assist in its functioning. (Such programming to set the configuration of the algorithm 220 may occur using an external system (FIG. 4) in communication with the IPG 100).

For example, the algorithm 220 can be programmed with an initialization period $t_i$ and a window period $t_w$. Initialization period $t_i$ comprises a duration during which the algorithm 220 will set control signal U to a default (e.g., '0') after an initialization event (Init). Such an initialization event can comprise starting stimulation (such as at time t0), a change in the stimulation (such as at t4 when the amplitude of the stimulation is increased), a change in the compliance voltage VH, a change in electrode impedances (which may be periodically measured during IPG 100 operation), starting sensing, or other still events. In this regard, notice that the algorithm 220 selects use of the low-voltage sense amp circuit 202a by default (U='0') after an initialization event. This is desired because as noted above the low-voltage diff amp 130 in sense amp circuit 202a would be less noisy, and hence is preferable to use if possible. The algorithm 220 may thereafter assess magnitude signal Z and eventually decide to either keep using the low-voltage sense amp circuit 202a or to switch to use of the high-voltage sense amp circuit 202b. The window period $t_w$ is useful in this regard. This period $t_w$ comprises a duration over which the algorithm 220 will assess the most-recent values of the magnitude signal Z. Although not shown, note that the data in magnitude signal Z is preferably time-stamped (e.g., by the control circuitry 102) to allow the algorithm 220 to understand which values of Z are recent enough to consider (i.e., which values fall within window period $t_w$).

The timing diagrams provide an example of how amplifier selection algorithm 220 can operate. At time t0 stimulation starts, which causes the algorithm 220 to initialize (Init). As noted, the algorithm 220 will automatically set control signal U to '0' for at least the initialization period i.e., until time t1. However, the algorithm 220 will also begin assessing the value of the magnitude signal Z. As described above, the monitoring circuitry 160 sets magnitude signal Z to '0' if the inputs X+ and X− are of a suitable magnitude to be handled by the low-voltage diff amp 130, and sets Z to '1' otherwise. It may be important for the algorithm 220 to consider the value of Z at particular times during the stimulation, and to ignore Z at other times. For example, when sensing stimulation artifacts, it may be most useful to consider Z during periods when stimulation is actually occurring (e.g., during actively-driven phases 30a and 30b). By contrast, when sensing neural responses, it may be most useful to consider Z after stimulation has ceased (e.g., during passive recharge 30c, or during quiet periods 30d; see FIG. 2A). In this regard, the algorithm 220 can also be programmed to receive information about the stimulation (Stim) to understand its timing and to allow the algorithm 220 to assess values of Z reported at times that are most relevant (and to ignore values of Z that are less relevant).

The timing diagrams in FIG. 7 are meant to show that the magnitude signal Z is essentially consistently '0' up until time t2. (Some occasional values of Z=1 are reported, which the algorithm 220 will likely interpret as noise or otherwise as insignificant). Thus, at time t1, the algorithm 220 assesses the most-recent values for Z (within window $t_w$), and decides to keep control signal U set at '0', which continues to use the low-voltage sense amp 202a for sensing, and this is true up until time t2.

At time t2 it is assumed that the magnitude signal Z is more consistently reporting a value of '1' (particularly during the stimulation pulses when the tissue voltage could be more significant) indicating that the voltages at X+ and/or X− are too high to be resolved by the low-voltage diff amp 130 in the low-voltage sense amp circuit 202a. Eventually at time t3, the algorithm 220 will understand Z to have been significantly high for long enough ($t_w$) that it now sets U='1' to select use of the high-voltage sense amp circuit 202b using switches 204a-206b.

In the example where the monitoring circuitry 160 is connected to the inputs of the low-voltage sense amp circuitry 202a as shown in FIG. 7, notice that selecting the high-voltage sense amp circuit 202b prevents the input signals X+ and X− from being assessed at the monitoring circuit 160 because they are cut off from the sensing electrode. As such, magnitude signal Z would be set to zero (or "don't care" values), and the high-voltage sense amp circuit 202b would be used until a next initialization event occurs (which as discussed above would select the low-voltage sense amp circuit 202a by default). This is reasonable because indications that higher voltages are present conservatively suggests that the high-voltage sense amp 202b should simply be used, even if this circuit consumes more power. (It may be counterproductive to thereafter switch back to use of the low-voltage sense amp 202a, or to continually switch between the two). However, this may not always by the case. For example, if the monitoring circuitry 160 is connected to the electrode nodes 39, or is additionally connected to the inputs of the high voltage sense amp circuit 202b (170; see FIG. 10), then magnitude signal Z may continuously issue regardless of the sense amp circuit 202a or 202b that is currently selected. This can allow the amplifier selection algorithm 220 to select the low-voltage sense amp circuit 202a again for use even after selection of the high-voltage sense amp circuit 202b, or otherwise to switch freely between them. Selecting the low-voltage sense amp circuit 202a can be beneficial as it will generally consume less power, and/or less noisy, than the high-voltage sense amp circuit 202b.

At time t4, it is assumed that the stimulation has changed, which can change the voltages in the tissue, and which can warrant (re)initializing the algorithm 220 (Init). Thus, at time t4, the algorithm 220 sets U to '0', again at least temporarily selecting use of the low-voltage sense amp circuit 202a. Because the values of Z continue to be relatively high and for a long enough duration (i.e., $t_w$), the algorithm 220 eventually sets U='1' at time t5 to select use of the high-voltage sense amp circuitry 202b, which in this example corresponds to the end of the initialization period ti set at time t4.

Thus, by use of the amplifier selection algorithm 220, the sense amp circuitry 200 can be controlled over time to eventually select the most appropriate of the sense amp circuits 202a or 202b, and to switch use of these circuits should the voltages in the tissue change. Furthermore, the algorithm 220 preferably selects the lower-noise low-voltage sense amp circuit 202a when possible. As the timing diagrams in FIG. 7 illustrate, such control is not immediate: some number of stimulation pulses may need to issue before the voltages at the sensing electrodes can be assessed (per Z), and use of the appropriate circuit 202a or 202b can be set (per U). However, such delay is generally not problematic to sensing neural responses. Even if it is desired to sense neural responses to improve the stimulation therapy the patient is receiving (per neural response algorithm 124 for example; FIG. 5), it is generally not necessary that such neural responses be sensed immediately. Moreover, and as discussed further below, even if the optimal sense amp circuit is not being used at a given moment, the monitoring circuit 160 can still provide magnitude signal Z to indicate whether a currently selected sense amp circuit (such as low-voltage sense amp circuit 202a) is outputting valid sensing data (and in this regard signal Z serves two functions, again as explained further below). It should be appreciated that FIG. 7 shows only one manner in which the low- or high-voltage sense amp circuits 202a or 202b can be selected using the magnitude of the voltage sensed at one or more of the inputs X+ or X−. Other approaches are possible, including approaches in which amplifier selection algorithm 220 operates differently, or operates as analog circuitry instead of as firmware digital logic.

As noted above, it may be useful to further process the analog outputs D+ and D− of the selected sense amp circuit 202a or 202b before they are digitized at the ADC 112, and optional back-end analog processing circuitry 210 is shown in FIG. 7 for this purpose. Processing circuitry 210 can include an additional diff amp 212 to add additional gain to the sensed signal. As shown, the gain of this diff amp 212 may be adjustable via gain control signals G3 issued by the IPG's control circuitry 102. In one example, the gain of diff amp 212 can be set to values of 1, 2, 4, 8, or 16 either in firmware or using an external system (FIG. 4) in communication with the IPG 100. Although not shown, still other additional diff amps 212 could be used in series to provide further gain to the sensed signal.

Track and hold circuitry 214 may also be included to hold the analog outputs D+ or D− (e.g., during the stimulation artifact 126 if that signal is not of interest), or to track these outputs. (Holding the analog outputs can be useful to prevent adverse operation of the filter 216, explained subsequently).

Attenuator 215 can be used to reduce the gain of the sensed signal if necessary. This may be particularly useful if it is desired to specifically sense the larger-signal stimulation artifact 126. (The amplifiers 202a, 202b, 212, etc. may impart too much gain to such a sensed signal, even when their gains are programmed to minimal values). The gain of the attenuator 215 can be programmed to a value less than or equal to 1 (e.g., 1 when sensing neural responses; 0.4 when sensing stimulation artifacts 126) via gain control signals G4, which can be programmed via firmware or using an external system (FIG. 4) in communication with the IPG 100. Note that the attenuator 215 may be considered as an amplifier in that it affects a gain of the sensed signal.

Lastly, filter circuitry 216 can also be included to remove frequencies from the sensed signal that are not of interest. Such excludable frequencies from the sensed signals may be low (such as those resulting from other biological processes such as respiration or heart rhythms) or high (such as noise). In this regard, filter 216 can comprise a band pass filter whose lower and upper frequencies ($f_L$, $f_H$) are programmable. Filter 216 could comprise a low pass filter, a high pass filter, or both. Low pass filtering in particular can be useful to providing anti-aliasing with respect to the sampling frequency used by the ADC 112.

Analog processing circuitry 210 is not strictly necessary, and any or all of stages 212-216 could be excluded. In this regard, the switches 206a and 206b could provide the differential output D+ and D− of the selected circuit 202a or 202b directly to the ADC 112, leaving it to the control circuitry 102 and/or the neural response algorithm 124 (FIG. 5) to digitally filter and process the signal as necessary. Analog processing circuitry 210 could also include additional stages not shown in FIG. 7.

The improved sense amp circuitry 200 of FIG. 7 is shown assuming that differential sensing is employed using two selected sensing electrodes (S+ and S−). However, one skilled will understand that the circuitry could be modified for single-ended sensing using only one sensing electrode (S) and one input (X) as well. As shown in dotted lines in FIG. 7, one of the inputs (e.g., X−) can be provided with a reference voltage as discussed earlier. Although only one sense amp circuit 220 is shown in FIG. 7 for simplicity, there could be more than one, such as a sense amp dedicated to each electrode node. In another example most useful for differential sensing, some number of sense amp circuitries 200 (e.g., four) can be provided, thus allowing any eight of the electrodes to be selected to act as sensing electrodes at a given time. Although not shown, one or more MUXes (e.g., 108, FIG. 5) can be provided to select the sensing electrodes and to provide their inputs X+ and X− to one of the sense amp circuits 200.

Figure 8:
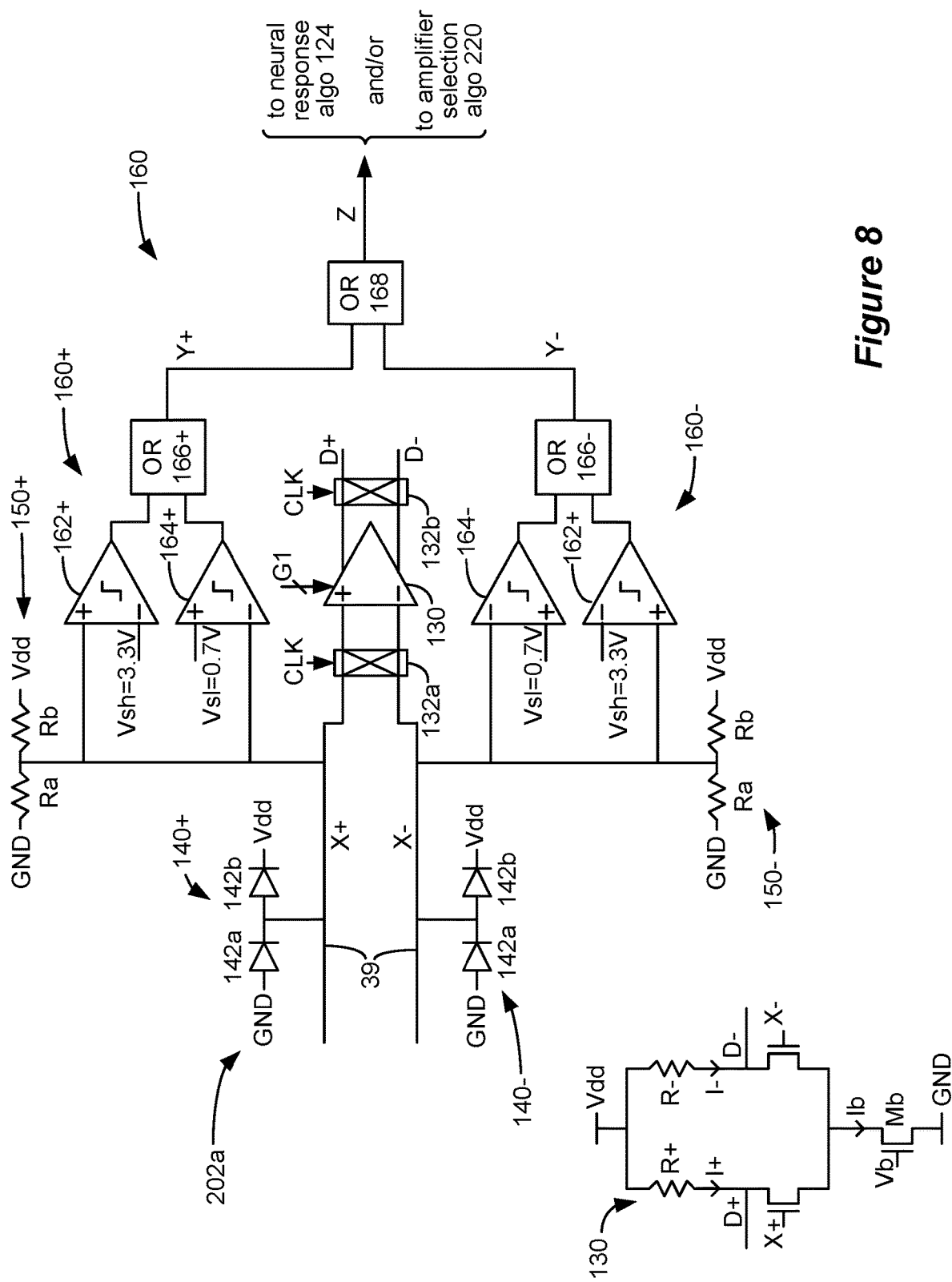
FIG. 8 shows details of the low-voltage sense amp circuit and monitoring circuitry that is used to assess the magnitude of at least one or both of the input signals, as useful to selecting use one of the sense amp circuits.

FIG. 8 shows details of the low-voltage sense amp circuit 202a and the monitoring circuitry 160. Many of the details shown in FIG. 8 are discussed in detail in U.S. Patent Application Publication 2020/0305744, which was incorporated above. Because the reader is assumed familiar with the '744 Publication, sense amp circuitry 202a and monitoring circuitry 160 are only briefly summarized here.

As discussed earlier, the low-voltage sense amp circuit 202a includes a low-voltage diff amp 130 which receives input signals X+ and X+ from the electrode nodes of the selected sensing electrodes S+ and S−, and which provides a differential output to analog outputs D+ and D− when the low-voltage sense amp circuit 202a is selected (i.e., U='0').

Diff amp 130 is a low-voltage diff amp powered by Vdd, which is assumed to equal 3.3 V, although this value could vary. The specific circuitry used for the low-voltage diff amp 130 can vary, but a simple example is shown at the lower left of FIG. 8. Preferably the gain of the diff amp 130 is programmable using control signals G1, and in one example the gain of the diff amp 130 can be adjusted from about 10 to 200. Gain control signals G1 can either be set in firmware or using an external system (FIG. 4) in communication with the IPG 100.

The diff amp 130 may be used in a well-known chopper amplifier configuration. Specifically, the inputs and outputs of the diff amp 130 can include polarity-reversing switches 132a and 132b control by a clock signal (CLK). As is known, switches 132a will switch the differential inputs (X+ and X−), thus modulating the inputs at the frequency of the clock signal. Switches 132b will likewise switch the differential outputs (D+ and D−), thus demodulating the amplified output back to a DC level. As is known, such "chopping" reduces noise, and in particular 1/f noise, which is helpful in resolving small-signal neural responses. That being said, chopping is not required when using the low-voltage diff amp 130, and switches 132a and 132b are optional. Still more preferably, chopping can be used (by providing the clock signal) if desired or not used (by setting the clock signal to '0').

To prevent damage to or improper operation of the diff amp 130, inputs X+ and X− are provided with clamping circuits 140+ and 140− respectively. In the example shown, these clamping circuits comprises a serial connection of diodes 142a and 142b which are forward biased between a low clamp reference voltage reference (ground in this example) and a high clamp reference voltage (Vdd=3.3V in this example), and with signals X+ and X− connected to a node between the diodes in 140+ and 140− respectively. As explained in the above-incorporated '744 Publication, and assuming the diodes 142a and 142b have a forward biased threshold voltage of 0.6V, X+ and X− are effectively clamped to a minimum of −0.6 Volts and a maximum of 3.9V Volts. In short, clamping circuits 140+ and 140− allow X+ and X− to pass to the inputs of the diff amp 130 without clamping if they are between −0.6 and 3.9 Volts, but otherwise clamps voltages on these signals from exceeding 3.9 Volts or from being lower than −0.6V. As explained in the '744 Publication, this protects the diff amp 130.

The sense amp circuit 202a further includes DC-level shifting circuits 150+ and 150− to reference signals X+ and X− to a DC voltage reference consistent with the input requirements for the diff amp 130. As discussed in the above-incorporated '744 Publication, the diff amp 130 can only operate reliably if input signals X+ and X− are of a magnitude that causes currents I+ and I− to flow in each leg of the amplifier 132 without saturating. In this regard, to properly sense, X+ and X− should be higher than the threshold voltage of the amplifier's input transistors M+ and M− (e.g., greater than Vtt=0.7 V), but less than the power supply voltage used to power the diff amp 130 (e.g., Vdd=3.3V). Accordingly, signals provided to the diff amp 130 are preferably referenced via circuits 150+/− to a DC voltage reference within this operating range. This reference could comprise ½Vdd (e.g., 1.65 V), ½(Vdd−Vtt)+Vtt (e.g., 2.0 V) in the middle of this operating range, or some other value within the operating range.

The magnitude of the DC voltage reference established by DC-level shifting circuits 150+/− can be set in different manners, but in the example shown they are set using a resistor ladder, comprising resistors Ra and Rb in series biased between Vdd and ground, with signals X+ and X− connected to nodes between the resistors. This sets the DC voltage reference of both X+ and X− to Ra/(Ra+Rb)*(Vdd−ground). In one simple example, Ra=Rb, which sets the DC voltage reference to ½Vdd. Preferably, Ra and Rb are large resistances to reduce current draw from the power supply Vdd, such 1 MegaOhm or higher.

Also connected to input signals X+ and X− is the monitoring circuitry 160 described earlier, which issues magnitude signal Z. This monitoring circuitry 160 is shown split into two pieces: 160+ for assessing the voltage on input X+, and 160− for assessing the voltage on input X−. However, in a single-ended sensing approach in which one of the inputs (e.g., X−) is held to a DC reference voltage, only one of these pieces (e.g., 160+) would be required. Circuits 160+ and 160− are similar, and 160+ is briefly discussed.

Circuitry 160+ includes comparators 164+ and 162+ which together comprise a window comparator to determine whether input X+ is between a low sense reference voltage Vsl and a high sense reference voltage Vsh. These references voltages Vsl and Vsh can be set by regulator circuitry as disclosed in the '744 Publication, and are set to values appropriate for proper diff amp 130 operation. Here it is assumed for simplicity that Vsl=Vtt (e.g., 0.7V) and Vsh=Vdd (e.g., 3.3V) respectively. Vsh may otherwise be determined relative to Vdd; for example it may differ from Vdd by a set amount. Again for simplicity, it is assumed that Vsh is set equal to Vdd (e.g., 3.3V).

If the magnitude of input X+ is between these voltages Vsl and Vsh, and hence at a magnitude suitable for diff amp 130 operation, both of comparators 162+ and 164+ output a '0'. If X+ is below 0.7V, i.e., too low to drive a current I+ in the diff amp 130, comparator 164+ outputs a '1'. If X+ is above 3.3V, i.e., too high for the diff amp 130 because current I+ would saturate, comparator 162+ outputs a '1'. These outputs can be logically ORed together at an OR gate 166+ to provide an output Y+ indicative of whether input X+ is at a magnitude for proper diff amp 130 operation (Y+='0' if 0.7V <X+<3.3V), or not (Y+='1' otherwise).

Note that it may not be required to determine whether input X+ is too low, especially if the diff amp 130 can handle low inputs. In this circumstance, comparator 164+ (and reference Vsl) and OR gate 166+ may not be necessary, and instead comparator 162+ may output Y+ directly.

Circuitry 160− is essentially the same, but indicates at output Y− whether input X− is at a suitable level (Y−='0') for proper diff amp 130 operation.

Outputs Y+ and Y− can be logically ORed by OR gate 186 to generate the magnitude signal Z described earlier, thus setting Z='0' if both of inputs X+ and X− are at proper magnitudes for diff amp operation 130, and setting Z='1' if either or both of inputs X+ and X− are at a magnitude unsuitable for proper diff amp operation 130.

Note that monitoring circuitry 160 can be associated with or comprise part of control circuitry 102. For example, and as discussed in the '744 Publication, analog-to-digital converters can sample and produce digital representations of inputs signals X+ and X−. These digital representations can be assessed and compared to thresholds (Vsl, Vsh) digitally to determine magnitude signal Z. In other words, monitoring circuitry 160 can be implemented using digital logic, and analog comparators circuits (162, 164) may not be necessary.

Note that the magnitude signal Z can be used for two purposes in the system. First, magnitude signal Z can provide the information necessary for the amplifier selection algorithm 220 (FIG. 7) to generate control signal U to select use of either of the sense amp circuits 202a or 202b as described previously. In this regard, note that magnitude signal Z as described may inform (Z='1') whether the input(s) are too low (<Vsl) or too high (>Vsh). As noted above, determining that an input is too low (the function of comparators 164+ and 164−) may not be required. An input being too low may not be relevant to the generation of control signal U as used to select a sense amp circuit 202a or 202b. In this regard, and although not shown in the figures, the amplifier selection algorithm 220 may receive other inputs to differentiate between a too-low or too-high condition. For example, the outputs of comparators 164+ and 164− may be provided to the algorithm 220 to understand whether Z=1 indicates too low or too high, and to ignore the former.

Second, and as described in detail in the above-incorporated '744 Publication, magnitude signal Z can inform the neural response algorithm 124 whether the sensed neural response is valid and reliable at a given time (Z='0') or not (Z='1'). Therefore, magnitude signal Z may be provided to both of these algorithms 220 and 124, as shown in FIG. 8. Using magnitude signal Z for both of these purposes is beneficial. As discussed above with reference to FIG. 7, control signal U may not necessarily immediately select the optimal sense amp circuit 202a or 202b (per control signal U). Nevertheless, even if a non-optimal circuit 202a or 202b is being used, magnitude signal Z can still inform the neural response algorithm 124 whether signal sensed by that circuit is valid at any given time. Hence, the neural response algorithm 124 can still consider reported neural responses detected by a non-optimal circuit 202a or 202b at least in part (i.e., when Z='0'), and can ignore reported neural responses at other times (when Z='1'). For example, if the data samples are marked as invalid (Z='1') during a transient (e.g., from a stimulation artifact), but as valid during an expected neural response (Z='0'), the data samples may be suitable for the neural response algorithm 124 to consider in resolving the neural response. By contrast, if the data samples are marked as invalid (Z='1') during an expected neural response, the data samples may be discarded or ignored by the algorithm 124.

Figure 9:
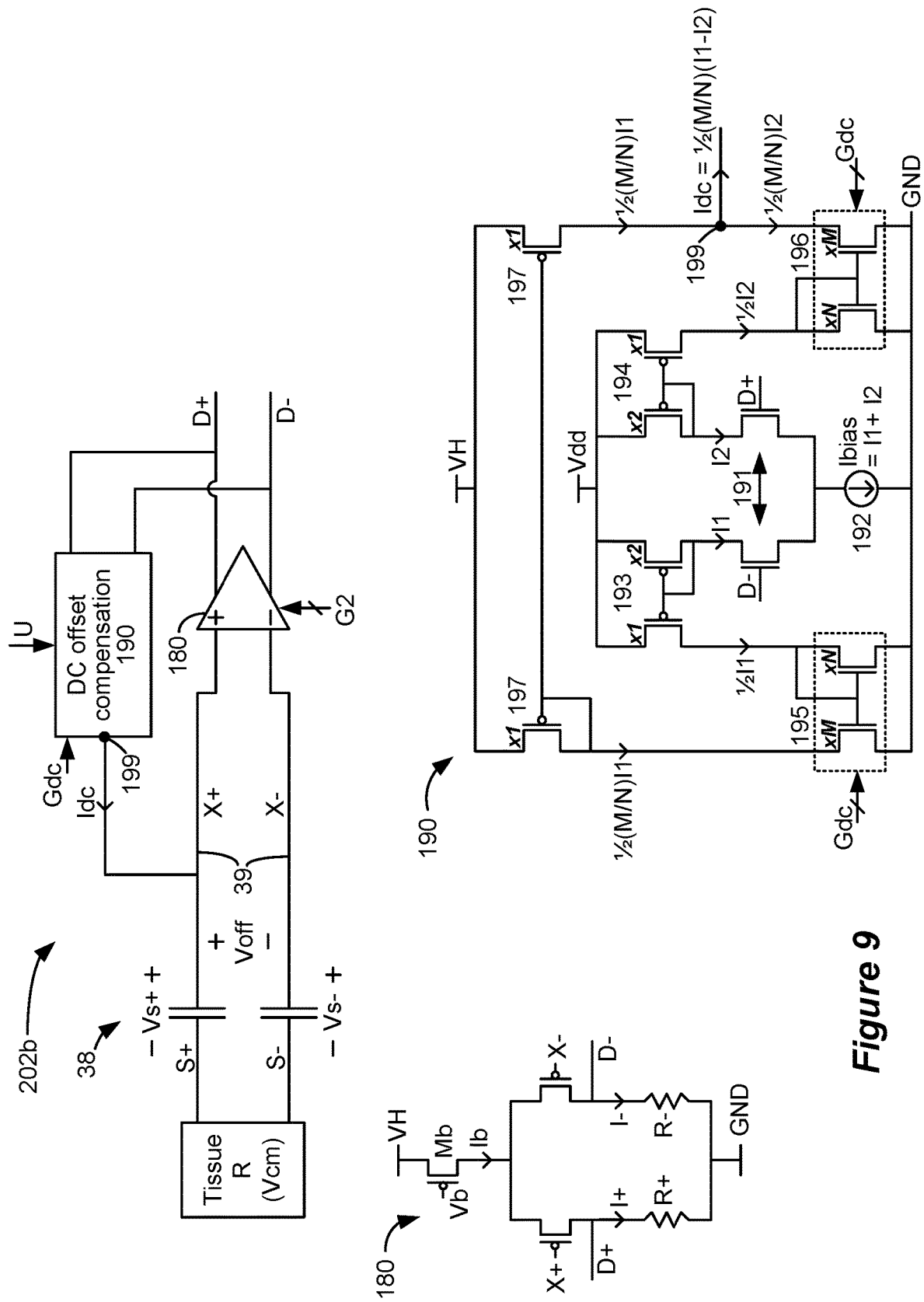
FIG. 9 shows details of the high-voltage sense amp circuit, including DC offset compensation circuitry that is used to remove any DC offset between the input signals.

FIG. 9 shows details of the high-voltage sense amp circuit 202b. As discussed earlier, the high-voltage sense amp circuit 202b includes a high-voltage diff amp 180 which receives input signals X+ and X+ from the electrode nodes of the selected sensing electrodes S+ and S−, and which provides a differential output to analog outputs D+ and D− when the high-voltage sense amp circuit 202b is selected (i.e., U='1'). Diff amp 180 is a high-voltage diff amp powered by the compliance voltage VH, which as noted earlier can vary. The specific circuitry used for the high-voltage diff amp 180 can vary, but a simple example is shown at the lower left of FIG. 9. Preferably the gain of the diff amp 180 is programmable using control signals G2, and in one example the gain of the diff amp 180 can be adjusted from about 1 to 100. Gain control signals G2 can either be set in firmware or using an external system (FIG. 4) in communication with the IPG 100.

Because the inputs X+ and X− are necessarily between VH and ground as explained previously, certain features described previously with respect to the low-voltage sense amp circuit 202a may not be necessary in the high-voltage sense amp circuit 202b and FIG. 9 shows these features removed. For example, clamping circuits (compare 140+ and 140− in FIG. 8) may not be connected to the inputs X+ and X−, because these inputs would not be expected to exceed VH. (Although not shown in FIG. 7, note that input switches 204a and 204b (FIG. 7) can be powered by VH. The transistors forming those switches would inherently clamp X+ and X− to VH, making clamping circuits 140+ and 140− unnecessary). DC-level shifting circuits (compare 150+ and 150− in FIG. 8) may also not be connected to the inputs X+ and X−, because the high-voltage diff amp 180 can receive a wide range of input voltages, making DC level adjustment unnecessary. That being said, the high-voltage sense amp circuit 202b could include clamping circuits and DC-level shifting circuits if desired.

Figure 10:
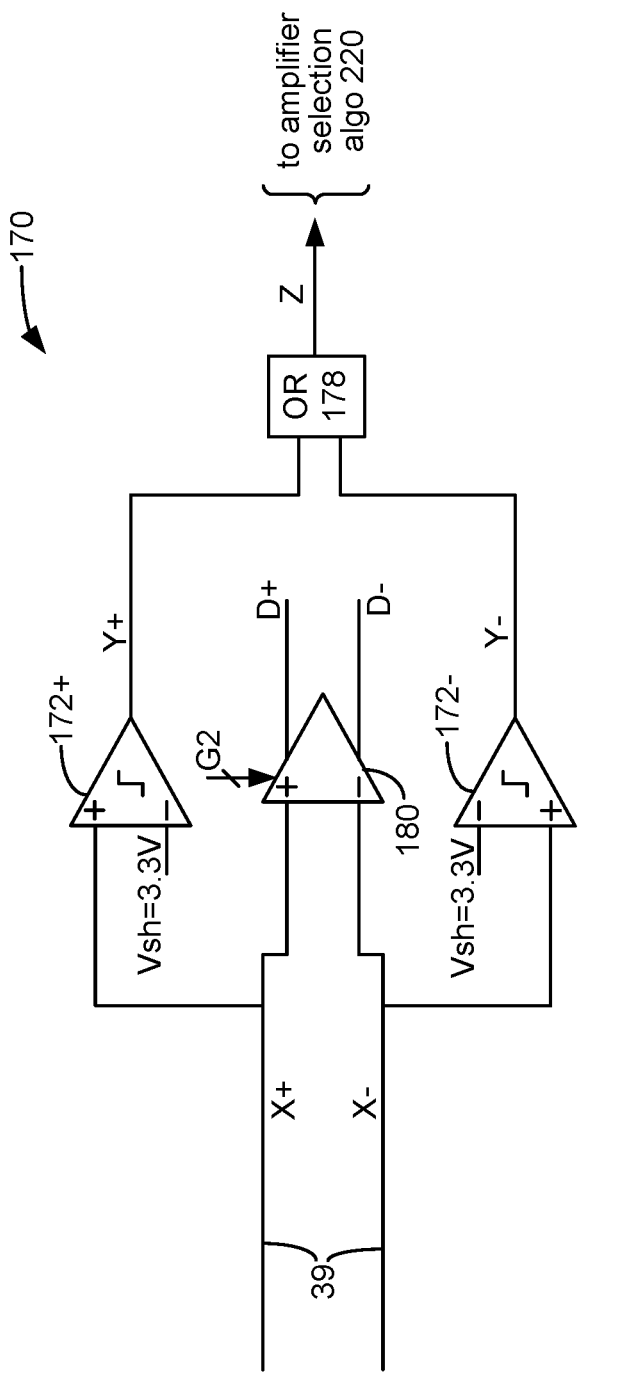
FIG. 10 shows an alternative in which the high-voltage sense amp circuit includes monitoring circuitry.

Further, monitoring circuitry (compare 160 in FIG. 8) may not be necessary when the high-voltage diff amp 180 is being used, because amp 180 should be able to handle the input voltages X+ and X−, therefore making an assessment of the level of these inputs less important. That being said, the high-voltage sense amp circuit 202b could monitoring circuitry, and an example 170 is shown in FIG. 10. Monitoring circuitry 170 is similar to the monitoring circuitry 160 described earlier, although in FIG. 10 it is designed to provide information to allow the amplifier selection algorithm 220 to switch from using the high-voltage sense amp circuit 202b back to the low-voltage sense amp circuit 202a should the magnitudes of the inputs X+ and X− drop to suitable levels. Thus, input X+ provides its input to a comparator 172+ that receives Vsh at its inverting input. In this example, Vsh=Vdd=3.3V. If X+ is larger than 3.3V, output Y+ is set to '1'; If X+ is smaller than 3.3V, Y+ is set to '0'. Comparator 172− sets output Y− similarly. Outputs Y+ and Y− can be ORed by OR gate 178 to output the magnitude signal Z assessed by the amplifier selection algorithm 220. If both of inputs X+ and X− are less than 3.3V, and hence suitable for input to the low-voltage sense amp circuit 202a, Z is set to '0', which can allow the algorithm 220 to (eventually) select use of circuitry 202a (by setting control signal U to '0'). If either of inputs X+ or X− is higher than 3.3V, Z is set to '1', which can allow the algorithm 220 to continue use of the high-voltage sense amp circuit 202b (by setting U to '1'). Thus, the algorithm 220 can switch between use of circuits 202a and 202b using both monitoring circuitry 160 (as described earlier) and monitoring circuitry 170. Note that these monitoring circuitries 160 and 170 can be considered a single monitoring circuit.

As also shown in FIG. 9, the VH sense amp circuit 202b preferably includes DC offset compensation circuitry 190. The goal of this circuitry is to equate the DC voltages at the inputs X+ and X− of the sense high-voltage diff amp 180. The difference in DC voltages at the inputs is generally not useful to sense (or amplify), as the diff amp 180 is generally concerned with sensing AC signals, such as neural responses and/or the stimulation artifact 126. DC offset compensation can also be an issue when sensing using the low-voltage diff amp 130 in the low-voltage sense amp circuit 202a (FIG. 8), but that diff amp 130 can more easily be designed to provide DC offset compensation on its own. This is more difficult to achieve in the high-voltage diff amp 180 which uses high-voltage and larger components. Thus, DC offset compensation circuitry 190 is preferably only used when the high-voltage sense amp circuitry 202b is selected (e.g., when U='1'). Thus, control signal U may be received at the DC offset compensation circuitry 190 to enable its use. Alternatively, another control signal (perhaps derived from U) can also be received at the circuitry 190. If the low-voltage diff amp 130 doesn't include DC offset compensation circuitry, circuitry 190 may also be used regardless whether the low- or high-voltage sense amp circuities 202a or 202b are used.

As noted, the goal of DC offset compensation circuitry 190 is to remove any differences in the DC voltages at the inputs to the diff amp 180. This offset is denoted by voltage Voff in FIG. 9, which may be positive or negative depending whether the voltage at V+ is higher or lower than the voltage at X−. Voff may result at least in part from differences to which the DC-blocking capacitors 38 at these electrode nodes 39 are charged, as represented by Vs+ and Vs−, which again may be positive or negative. Said simply, the goal of DC offset compensation circuitry 190 is to reduce the DC level of Voff, preferably to zero. Note that Vs+ and Vs− may be referenced to a common mode voltage in the tissue, Vcm. Such a common mode voltage may be inherent in the tissue, or established by the IPG. For example, Vcm can be formed specifically by biasing circuitry in the IPG 100 at a given electrode, such as the case electrode Ec or another lead-based electrode that is not being used to provide stimulation, as explained in the above-incorporated U.S. Pat. No. 11,040, 202.

DC offset compensation is accomplished by assessing the DC offset of the differential analog output D+ and D−, and converting this difference to a current Idc that is used to adjust Vs+ across the DC-blocking capacitor in series with input X+. In other words, the goal of circuitry 190 is to adjust Vs+ via current Idc until Voff equals zero. This would likely set Vs+ equal to Vs−, especially if different charges on the DC-blocking blocking capacitors are solely response for the DC offset Voff. Although not shown, note that current Idc could also be provided to the other input X− to adjust Vs−. Preferably, Idc is on the order of nanoAmps, which is very small in comparison to the magnitude of the stimulation currents provided to the electrodes. In this respect, Idc does not appreciably contribute to stimulation of the patient's tissue.

An example of DC offset compensation circuitry 190 is shown in FIG. 9. As shown, this circuitry 190 receives the outputs D+ and D− as output by the high-voltage diff amp 180. However, other representations of this output present along analog processing circuitry 210 (FIG. 7) could also be input to circuitry 190. For example, the outputs of additional diff amps like 212 in circuitry 210 (FIG. 7) could be provided to the inputs of the circuitry 190, thus allowing the offset circuitry 190 to operate on an output DC voltage difference that is larger (because this difference is amplified by 212).

Regardless of where the differential output voltages are tapped, they are input to transistors 191. These transistors 191 are coupled to a programmable current source 193, which produces a current of Ibias, which may be programmable. Ibias must necessarily comprise the current as drawn through both of transistors 191, i.e., Ibias=I1+I2. These currents I1 and I2 will scale with the magnitude of the voltage on the transistors. Thus, if the DC voltage at D+ is larger than D− (which would imply that the DC offset voltage Voff is positive, and hence that Vs+ is larger than Vs−), then I2>I1. By contrast, if the DC voltage at D− is larger than D+ (which would imply that the voltage Voff is negative, and hence that Vs− is larger than Vs+), then I1>I2.

Currents I1 and I2 are reflected through a number of current mirrors, which as one skilled understand comprises circuits having transistors whose gates are shorted, and with that shorted gate also connected to the input current. For example, current mirror transistors 193 mirror current I1 to an output branch. The current mirror transistors 193 can comprise a number of similar transistors wired in parallel to set a scalar for the current in the output branch. As shown, the input branch includes two transistors 193 in parallel (×2), while the output branch includes only one transistor 193 (×1). This sets the current in the output branch to ½I1.

This output current ½I1 is itself input to another current mirror formed of transistors 195. These transistors 195 have a programmable number of paralleled transistors that can be included in the input (×N) and output (×M) branches. The number of transistors M and N can be programmed in accordance with gain control signals Gdc to produce a current in the output branch of ½(M/N)I1. Although not shown, these gain control signals Gdc can set N and M individually, with N programmable to values of 1, 4, 16, and 64, and M programmable to 1 or 20. Gain control signals Gdc can either be set in firmware or using an external system (FIG. 4) in communication with the IPG 100.

This output current ½(M/N)I1 is itself input to another current mirror formed of transistors 197. These transistors have the same number of paralleled transistors (×1), and so the output branch outputs this current ½(M/N)I1 to node 199 from which Idc issues.

Current I2 is similarly mirrored through similar circuitry. Current mirror transistors 194 mirror current I2, and given the scaling based upon the number of transistors used, outputs ½I2 in its output branch. This output current ½I2 is itself input to another current mirror formed of transistors 196, which as before can use of a number of transistors N and M as set by the gain control signals Gdc. This produces a current of ½(M/N)I2 in the output branch at node 199. Node 199 also outputs current Idc to node X+, which results from any imbalance between currents ½(M/N)I1 provided to node 199, and current ½(M/N)I2 drawn from node 199. More specifically, Idc=½(M/N)(I1−I2).

Operation of DC offset compensation circuitry 190 can be understood by consider different values for Voff. Assume Voff is zero, meaning that the DC voltages at X+ and X− are equal, presumably because Vs+ is equal to Vs−. After amplification (180), the DC voltages of D+ and D− would also be equal. These voltages at D+ and D− are inputs to transistors 191 in the DC offset compensation circuitry 190, and because these voltages are the same, I1=I2. This means that current Idc equals zero. This leaves the DC-blocking capacitor 38 at input X+ unaffected—i.e., it is not charged or discharged—and Vs+ remains unaffected.

However, if Voff is positive, this means that the DC voltage at X+ is higher than at X−, presumably because Vs+ is larger than Vs−. After amplification (180), the DC voltage of D+ would be higher than at D−. The voltages at D+ and D− are inputs to transistors 191 in the DC offset compensation circuitry 190, resulting in I2 being higher than I1, as previously discussed. This means the current Idc as defined in FIG. 9 is negative. This will discharge the DC-blocking capacitor 38 at input X+, which will reduce Vs+ and bring Voff closer to zero.

If Voff is positive, this means that the DC voltage at X+ is lower than at X−, presumably because Vs+ is smaller than Vs−. After amplification (180), the DC voltage of D+ would be lower than at D−. The voltages at D+ and D− are input to transistors 191 in the DC offset compensation circuitry 190, resulting in I1 being higher than I2, as previously discussed. This means the current Idc as defined in FIG. 9 is positive. This will charge the DC-blocking capacitor 38 at input X+, which will raise Vs+ and bring Voff closer to zero.

In short, as the DC offset compensation circuitry 190 operates, feedback will eventually set Voff equal to zero by eventually charging or discharging the DC blocking capacitor 38 coupled to input X+, presumably to a level where Vs+ equal Vs−. Note that the DC offset compensation circuitry 190 can operate whether differential or single ended sensing is used. For example, if single-ended sensing is used, input X− can be connected to a constant reference voltage (e.g., Vref; see FIG. 7). In this case, operation of the circuitry 190 will bring the DC voltage at input X+ to Vref by creating a current Idc and charging or discharging the capacitor (Vs+) as necessary.

Note that the speed with which DC offset compensation occurs—i.e., the speed at which Voff is set to zero—is strongly influenced by the magnitude of Idc. Larger values of Idc will charge or discharge the DC-blocking capacitor at input X+ (Vs+) faster. (Further, the speed will depend on the RC time constant involved—i.e., the capacitance of the DC-blocking capacitors and inherent resistances, such as those in the tissue R and the electrodes). The magnitude of Idc can be increased using gain control signal Gdc. For example, the gain control signals Gdc can be used to increase M, or decrease N (i.e., the number of paralleled transistors present in current mirrors 195 and 196), either of which would increase Idc.

However, it may not always be warranted to cause DC offset compensation to occur as quickly as possible. Setting DC offset compensation to occur quickly will also affect the frequencies of AC signals that can be sensed. Generally speaking, faster DC offset compensation (larger Idc) will prevent the sense amp circuitry 200 from sensing lower frequency AC events, because faster compensation will effectively cancel such low-frequency AC events at the inputs X+ and X−. In this regard, the DC offset compensation circuitry 190 in effect operates a high pass filter, with larger values of Idc (as set by Gdc) increasing the cutoff frequency. Thus, using a high Idc may cause potentially-interesting low-frequency AC events to be compensated for, preventing them from being sensed. If it is desired to sense such low-frequency events in a given application (e.g., DBS), it may be warranted to adjust Idc via Gdc to allow DC offset compensation to occur more slowly—i.e., by reducing M or increasing N.

As noted earlier, an ECAP is just one example of a neural response that can be sensed using the disclosed sense amp circuits. Not all neural responses one might desire to sense are a result of stimulation, and in this regard the disclosed sense amp circuits can be used in an implantable device that may not include stimulation circuitry 28 (FIG. 3). Furthermore, the disclosed sense amp circuits can be used to sense other types of signals in the tissue beyond neural responses. For example, the sense amp circuitry could be used to sense other types of signals, such as those used for measuring tissue field potentials or tissue resistance.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A stimulator device, comprising:
 a plurality of electrode nodes, wherein each of the electrode nodes is associated with a different electrode configured to contact a patient's tissue, wherein at least one of the electrodes comprises a sensing electrode to receive a voltage from the tissue, wherein each electrode node associated with the at least one sensing electrode comprises a sensing electrode node;
 sense amplifier circuitry comprising a first amplifier with a first input and a first output and a second amplifier with a second input and a second output; and
 monitoring circuitry configured to assess a voltage at each sensing electrode node, wherein the monitoring circuitry is configured based on the assessed one or more voltages to select use of the first or the second amplifier to determine a signal in the tissue.

2. The stimulator device of claim 1, further comprising input switching circuitry between each sensing electrode node and the first input and between each sensing electrode node and the second input,
 wherein the monitoring circuitry is configured to select the first or the second amplifier by controlling the input switching circuitry to either connect each sensing electrode node to the first input or to the second input.

3. The stimulator device of claim 2, further comprising an analog-to-digital converter (ADC), wherein the ADC is configured to provide a digitized representation of the determined signal; and
 output switching circuitry between the first output and the ADC and between the second output and the ADC,
 wherein the monitoring circuitry is configured to select the first or the second amplifier by controlling the output switching circuitry to either couple the first output to communicate with the ADC or to couple the first output to communicate with the ADC.

4. The stimulator device of claim 1, further comprising processing circuitry, wherein the coupled first or second output communicates with the ADC via the processing circuitry.

5. The stimulator circuitry of claim 4, wherein the processing circuitry comprises one or more of an additional amplifier to impart a gain to the first or second output of the selected first or second amplifier, and filter circuitry to filter the first or second output of the selected first or second amplifier.

6. The stimulator device of claim 1, wherein the first amplifier is powered by a first power supply voltage, and wherein the second amplifier is powered by a second power supply voltage higher than the first power supply voltage.

7. The stimulator device of claim 6, further comprising stimulation circuitry configured to provide stimulation to one or more of the electrode nodes to provide stimulation to the patient's tissue via associated stimulation electrodes.

8. The stimulator device of claim 7, wherein the stimulation electrodes are different from the at least one sensing electrode.

9. The stimulator device of claim 7, wherein the stimulation circuitry is powered by the second power supply voltage.

10. The stimulator device of claim 1, wherein the monitoring circuitry is configured to assess the voltage at each sensing electrode node by comparing the voltage at each sensing electrode node to a first voltage.

11. The stimulator device of claim 10, wherein the monitoring circuitry is configured to select the first amplifier if the voltage at each sensing electrode node is below the first voltage.

12. The stimulator device of claim 10, wherein the monitoring circuitry is configured to select the second amplifier if the voltage at any sensing electrode node is above the first voltage.

13. The stimulator device of claim 10, wherein the first amplifier is powered by a first power supply voltage, wherein the first voltage is set relative to the first power supply voltage.

14. The stimulator device of claim 13, wherein the first voltage equals the first power supply voltage.

15. The stimulator device of claim 1, wherein the monitoring circuitry is further configured upon the occurrence of an initialization event to select the use of the first amplifier during an initialization period.

16. The stimulator device of claim 1, wherein the monitoring circuitry comprises an algorithm to assess the voltage at each sensing electrode node, wherein the algorithm is configured to generate a control signal based on the assessed voltages to select the use of the first or the second amplifier.

17. The stimulator device of claim 1, further comprising a DC-blocking capacitance between each of the electrode nodes and its associated electrode.

18. The stimulator device of claim 1, wherein the first amplifier and the second amplifier comprise differential amplifiers, wherein the first input comprises a first differential input, and wherein the second input comprises a second differential input.

19. The stimulator device of claim 18, wherein two of the electrodes comprise the sensing electrodes to receive the voltage from the tissue, wherein two sensing electrode nodes are associated with the two sensing electrodes, wherein the monitoring circuitry is configured to assess the voltages at the two sensing electrode nodes, wherein the monitoring circuitry is configured based on the assessed voltages to select the use of the first or the second amplifier by respectively connecting the two sensing electrode nodes to the first differential input or the second differential input.

20. The stimulator device of claim 18, wherein only one of the electrodes comprises the sensing electrode to receive the voltage from the tissue, wherein one sensing electrode node is associated with the sensing electrode, wherein the monitoring circuitry is configured to assess the voltage at the one sensing electrode node, wherein the monitoring circuitry is configured based on the assessed voltage to select the use of the first or the second amplifier by respectively connecting the sensing electrode node to the first differential input or the second differential input, wherein the sensing electrode node is compared to a reference voltage of the selected first or second amplifier.

* * * * *